United States Patent
Azizian

(10) Patent No.: US 12,186,035 B2
(45) Date of Patent: Jan. 7, 2025

(54) SYSTEMS AND METHODS FOR TAG-BASED INSTRUMENT CONTROL

(71) Applicant: Intuitive Surgical Operations, Inc., Sunnyvale, CA (US)

(72) Inventor: Mahdi Azizian, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/010,560

(22) PCT Filed: Jun. 28, 2021

(86) PCT No.: PCT/US2021/039342
§ 371 (c)(1),
(2) Date: Dec. 15, 2022

(87) PCT Pub. No.: WO2022/005954
PCT Pub. Date: Jan. 6, 2022

(65) Prior Publication Data
US 2023/0225804 A1 Jul. 20, 2023

Related U.S. Application Data

(60) Provisional application No. 63/046,251, filed on Jun. 30, 2020, provisional application No. 63/046,278, filed on Jun. 30, 2020.

(51) Int. Cl.
*G06F 3/048* (2013.01)
*A61B 34/00* (2016.01)
*G06F 3/0484* (2022.01)

(52) U.S. Cl.
CPC .............. *A61B 34/25* (2016.02); *G06F 3/0484* (2013.01); *A61B 2034/254* (2016.02)

(58) Field of Classification Search
CPC ............................. A61B 34/25; G06F 3/0484
See application file for complete search history.

(56) References Cited

U.S. PATENT DOCUMENTS

| 2006/0058616 | A1 | 3/2006 | Marquart et al. |
| 2017/0245940 | A1* | 8/2017 | Piron .................... G06T 7/30 |
| 2018/0082480 | A1 | 3/2018 | White et al. |

(Continued)

FOREIGN PATENT DOCUMENTS

| WO | WO-2017098503 A1 | 6/2017 |
| WO | WO-2017098505 A1 | 6/2017 |
| WO | WO-2019036318 A2 | 2/2019 |

OTHER PUBLICATIONS

International Preliminary Report on Patentability for Application No. PCT/US2021/039342 mailed Jan. 12, 2023, 16 pages.

(Continued)

*Primary Examiner* — Claudia Dragoescu

(57) ABSTRACT

A system may render, within a graphical user interface associated with a computer-assisted medical system, a graphical tag element associated with a physical location within a region of interest. The system may detect a user interaction with the graphical tag element. The system may further direct, in response to the detecting of the user interaction with the graphical tag element, the computer-assisted medical system to adjust a pose of an instrument based on the physical location within the region of interest.

20 Claims, 20 Drawing Sheets

(56) References Cited

U.S. PATENT DOCUMENTS

| | | | |
|---|---|---|---|
| 2018/0214214 A1* | 8/2018 | Reinstein | A61B 5/066 |
| 2019/0247126 A1* | 8/2019 | Ikehara | A61B 1/043 |
| 2019/0374288 A1 | 12/2019 | Palushi et al. | |
| 2020/0110936 A1* | 4/2020 | Hares | A61B 1/3132 |
| 2021/0186460 A1* | 6/2021 | Meglan | A61B 8/463 |

OTHER PUBLICATIONS

International Search Report and Written Opinion for Application No. PCT/US2021/039342, mailed Jan. 31, 2022, 22 pages.
Partial International Search Report for PCT/US2021/039342, mailed Oct. 25, 2021, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

SYSTEMS AND METHODS FOR TAG-BASED INSTRUMENT CONTROL

RELATED APPLICATIONS

The present application is a U.S. National Stage Application under 35 U.S.C. § 371 of International Application No. PCT/US2021/039342, filed on Jun. 28, 2021, which claims priority to U.S. Provisional Patent Application No. 63/046,278, filed Jun. 30, 2020, the contents of which are hereby incorporated by reference in their entirety. International Application No. PCT/US2021/039342 also claims priority to U.S. Provisional Patent Application No. 63/046,251, filed Jun. 30, 2020, the contents of which are hereby incorporated by reference in their entirety.

BACKGROUND INFORMATION

An imaging device may be used during a medical procedure to capture images of a region of interest. The images may be presented to a user to assist the user in performing the medical procedure. For example, an endoscopic video feed showing a surgical area of a patient may be presented to a surgeon during a minimally-invasive surgical procedure to assist the surgeon in performing the surgical procedure. During a medical procedure, an event may occur at a specific location within the region of interest. However, it can be difficult for a user to keep of track of the event during the medical procedure and the location where the event occurred, particularly when the region of interest has many moving parts, such as patient tissue, medical tools, and surgical instruments. In some cases, the user may not even be aware that the event has occurred.

SUMMARY

The following description presents a simplified summary of one or more aspects of the methods and systems described herein in order to provide a basic understanding of such aspects. This summary is not an extensive overview of all contemplated aspects and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to render, within a graphical user interface associated with a computer-assisted medical system, a graphical tag element associated with a physical location within a region of interest; detect a user interaction with the graphical tag element; and direct, in response to the detecting of the user interaction with the graphical tag element, the computer-assisted medical system to adjust a pose of an instrument based on the physical location within the region of interest.

An exemplary method may comprise rendering, by a tagging system within a graphical user interface associated with a computer-assisted medical system, a graphical tag element associated with a physical location within a region of interest; detecting, by the tagging system, a user interaction with the graphical tag element; and directing, by the tagging system in response to the detecting of the user interaction with the graphical tag element, the computer-assisted medical system to adjust a pose of an instrument based on the physical location within the region of interest.

An exemplary non-transitory computer-readable medium may store instructions that, when executed, direct at least one processor of a computing device to render, within a graphical user interface associated with a computer-assisted medical system, a graphical tag element associated with a physical location within a region of interest; detect a user interaction with the graphical tag element; and direct, in response to the detecting of the user interaction with the graphical tag element, the computer-assisted medical system to adjust a pose of an instrument based on the physical location within the region of interest.

Another exemplary system may comprise a memory storing instructions and a processor communicatively coupled to the memory and configured to execute the instructions to render, at a current time within a graphical user interface associated with a computer-assisted medical system, a graphical tag element associated with a physical location within a region of interest, the graphical tag element being representative of an event that occurred within the region of interest at a prior time prior to the current time; detect a user interaction with the graphical tag element; and direct, in response to the detecting of the user interaction with the graphical tag element, the computer-assisted medical system to adjust a current field of view of an imaging device based on the physical location within the region of interest to match a prior field of view of the imaging device when the event occurred.

Another exemplary system may comprise a memory storing instructions and a processor communicatively coupled to the memory and configured to execute the instructions to access medical session data for a medical session, the medical session including performance of one or more operations by a computer-assisted medical system; determine, based on the medical session data, that an event occurs within a region of interest associated with the medical session; identify a physical location within the region of interest and associated with the event; identify content depicting the physical location when the event occurred; associate the content with the physical location; and provide, after the event occurs, a user with access to the content when the physical location is within a field of view of an imaging device.

Another exemplary system may comprise a memory storing instructions and a processor communicatively coupled to the memory and configured to execute the instructions to access a fluorescence image stream generated based on fluorescence signals detected from a region of interest associated with a surgical session, the surgical session including performance of one or more operations by a computer-assisted surgical system; determine, based on the fluorescence image stream, that a fluorescence event occurs at the region of interest during the surgical session, the fluorescence event comprising a detection that a contrast level of a fluorescence image included in the fluorescence image stream is within a predefined range; identify a physical location within the region of interest and associated with the fluorescence event; associate the fluorescence image with the physical location; and provide, after the event occurs, a user with access to view the fluorescence image when the physical location is within a field of view of an imaging device.

Another exemplary method may comprise accessing, by a tag management system, medical session data for a medical session, the medical session including performance of one or more operations by a computer-assisted medical system; determining, by the tag management system and based on the medical session data, that an event occurs within a region of interest associated with the medical session; identifying, by the tag management system, a physical location within the region of interest and associated with the event; identifying, by the tag management system, content depicting the physical location when the event occurred; associating, by the tag management system, the content with the physical location; and providing, after the event occurs, a user with access to the content when the physical location is within a field of view of an imaging device.

Another exemplary non-transitory computer-readable medium may store instructions that, when executed, direct at least one processor of a computing device to access medical session data for a medical session, the medical session including performance of one or more operations by a computer-assisted medical system; determine, based on the medical session data, that an event occurs within a region of interest associated with the medical session; identify a physical location within the region of interest and associated with the event; identify content depicting the physical location when the event occurred; associate the content with the physical location; and provide, after the event occurs, a user with access to the content when the physical location is within a field of view of an imaging device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for tag-based instrument control are described herein. Also described herein are systems and methods for providing access to event-based content with spatial memory. Various specific embodiments will be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein may provide one or more benefits that will be explicitly described or made apparent below.

Figure 1:
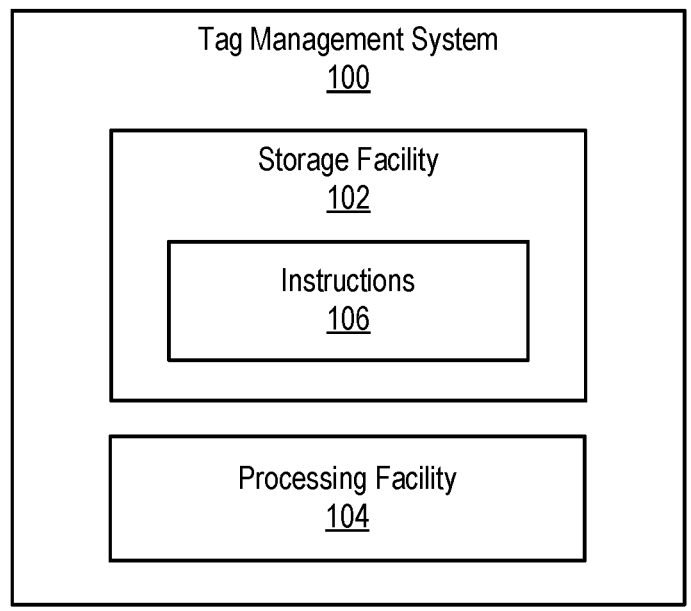
FIG. 1 illustrates an exemplary tag management system according to principles described herein.

FIG. 1 illustrates an exemplary tag management system 100 ("system 100"). System 100 may be included in, implemented by, or connected to any medical system or other computing system described herein. For example, system 100 may be implemented by a computer-assisted medical system. As another example, system 100 may be implemented by a stand-alone computing system communicatively coupled to a computer-assisted medical system.

As shown, system 100 includes, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and 104 may be implemented by any component in a computer-assisted medical system. In some examples, facilities 102 and 104 may be distributed between multiple devices and/or multiple locations as may serve a particular implementation.

Storage facility 102 may maintain (e.g., store) executable data used by processing facility 104 to perform any of the operations described herein. For example, storage facility 102 may store instructions 106 that may be executed by processing facility 104 to perform any of the operations described herein. Instructions 106 may be implemented by any suitable application, software, code, and/or other executable data instance. Storage facility 102 may also maintain any data received, generated, managed, used, and/or or transmitted by processing facility 104.

Processing facility 104 may be configured to perform (e.g., execute instructions 106 stored in storage facility 102 to perform) various operations described herein. It will be recognized that the operations and examples described herein are merely illustrative of the many different types of operations that may be performed by processing facility 104. In the description herein, any references to operations performed by system 100 may be understood to be performed by processing facility 104 of system 100. Furthermore, in the description herein, any operations performed by system 100 may be understood to include system 100 directing or instructing another computing system or computing device to perform the operations.

As mentioned, system 100 may be implemented as part of or in conjunction with a medical system, such as a computer-assisted medical system. As such, an exemplary computer-assisted medical system will now be described. The following exemplary computer-assisted medical system is illustrative and not limiting, as the systems and methods described herein may be implemented as part of or in conjunction with other suitable medical systems.

Figure 2:
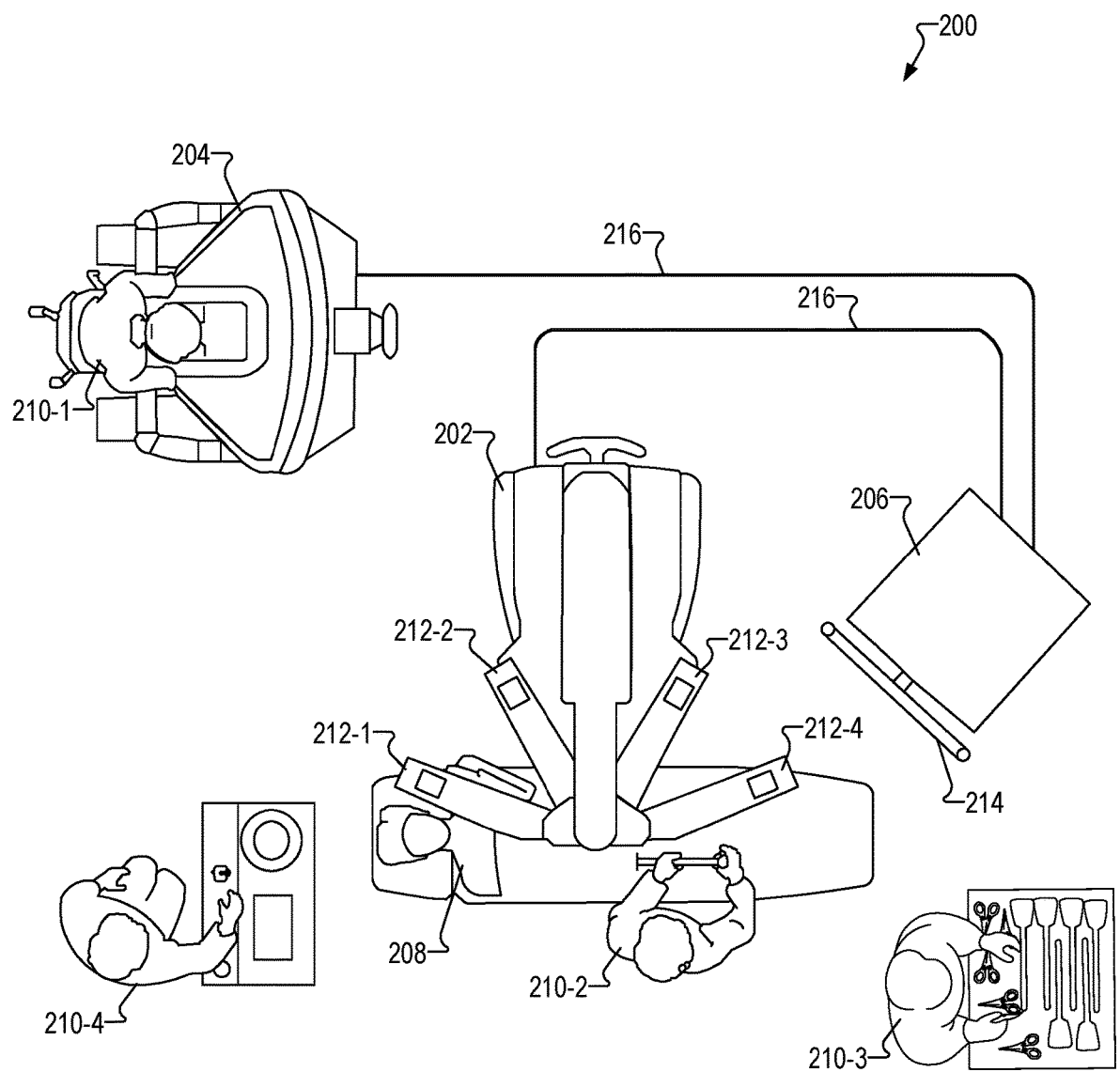
FIG. 2 illustrates an exemplary computer-assisted surgical system according to principles described herein.

FIG. 2 illustrates an exemplary computer-assisted surgical system 200 ("surgical system 200"). As shown, surgical system 200 may include a manipulating system 202, a user control system 204, and an auxiliary system 206 communicatively coupled one to another. In some examples, surgical system 200 may be implemented by one or more of these components. However, surgical system 200 is not limited to these components, and may include additional components as may suit a particular implementation, such as but not limited to a patient operating table, third-party components (e.g., electrosurgical units) connected to surgical system 200, and the like.

Surgical system 200 may be utilized by a surgical team to perform a computer-assisted surgical procedure on a patient 208. As shown, the surgical team may include a surgeon 210-1, an assistant 210-2, a nurse 210-3, and an anesthesiologist 210-4, all of whom may be collectively referred to as "surgical team members 210." Additional or alternative surgical team members may be present during a surgical session as may serve a particular implementation.

While FIG. 2 illustrates an ongoing minimally invasive surgical procedure, surgical system 200 may similarly be used to perform open surgical procedures or other types of surgical procedures that may similarly benefit from the accuracy and convenience of surgical system 200. Additionally, it will be understood that a surgical session throughout which surgical system 200 may be employed may not only include an operative phase of a surgical procedure, as is illustrated in FIG. 2, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any non-clinical procedure, e.g., a procedure that is not performed on a live patient, such as a calibration or testing procedure, a training procedure, and an experimental or research procedure.

As shown in FIG. 2, manipulating system 202 may include a plurality of manipulator arms 212 (e.g., manipulator arm 212-1 through 212-4) to which a plurality of surgical instruments (not shown in FIG. 2) may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 208 and manipulated to perform a computer-assisted surgical procedure on patient 208). In some examples, one or more of the surgical instruments may include force-sensing and/or other sensing capabilities. While manipulating system 202 is depicted and described herein as including four manipulator arms 212, it will be recognized that manipulating system 202 may include only a single manipulator arm 212 or any other number of manipulator arms as may serve a particular implementation.

Manipulator arms 212 and/or surgical instruments attached to manipulator arms 212 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 212, surgical instruments coupled to manipulator arms 212, and/or any other components of manipulating system 202 (e.g., boom arms). One or more components of surgical system 200 may be configured to use the kinematics information to track (e.g., determine poses, movements, and/or states of) and/or control manipulator arms 212 and/or surgical instruments. Manipulating system 202 may also include other sensors configured to generate other information as may suit a particular implementation. Such sensors may also be referred to as "surgical system sensors" and may include, for example, draping sensors, boom height sensors, and the like.

Surgical instruments attached to manipulator arms 212 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 200 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 204 may be configured to facilitate user control of surgical system 200 (e.g., manipulator arms 212 and surgical instruments attached to manipulator arms 212). For example, surgeon 210-1 may interact with user input devices included in user control system 204 to remotely move or manipulate manipulator arms 212 and the surgical instruments coupled to manipulator arms 212. To this end, user control system 204 may provide surgeon 210-1 with imagery (e.g., high-definition stereoscopic imagery) of a surgical area associated with patient 208 as captured by an imaging device (e.g., a stereoscopic endoscope). Surgeon 210-1 may utilize the imagery to perform one or more procedures with one or more surgical instruments coupled to manipulator arms 212.

To facilitate control of surgical instruments, user control system 204 may include a set of master controls (not shown in FIG. 2). These master controls may be manipulated by surgeon 210-1 to control movement of surgical instruments (e.g., by utilizing robotic and/or teleoperation technology). The master controls may be configured to detect a wide variety of hand, wrist, and finger movements by surgeon 210-1. In this manner, surgeon 210-1 may intuitively perform a surgical procedure using one or more surgical instruments.

User control system 204 may further be configured to facilitate control of other components of surgical system 200. For example, surgeon 210-1 may interact with user control system 204 to change a configuration or operating mode of surgical system 200, to change a display mode of surgical system 200, to generate additional control signals used to control surgical instruments attached to manipulator arms 212, to facilitate switching control from one surgical instrument to another, or to perform any other suitable operation. To this end, user control system 204 may also include one or more additional user input devices (e.g., foot pedals, buttons, switches, touchscreen displays, etc.) configured to receive manual input from surgeon 210-1. In some examples, user control system 204 may also include one or more audio input devices (e.g., microphones) configured to receive audio input (e.g., voice input) from one or more users, and one or more audio output devices (e.g., speakers).

Auxiliary system 206 may include one or more computing devices configured to perform primary processing operations of surgical system 200. The one or more computing devices included in auxiliary system 206 may control and/or coordinate operations performed by various other components (e.g., manipulating system 202 and/or user control system 204) of surgical system 200. For example, a computing device included in user control system 204 may transmit instructions to manipulating system 202 by way of the one or more computing devices included in auxiliary system 206. As another example, auxiliary system 206 may receive, from manipulating system 202 (e.g., from an imaging device), and process image data representative of imagery captured by an endoscope attached to a manipulator arm 212.

In some examples, auxiliary system 206 may be configured to present visual content to surgical team members 210 who may not have access to the imagery provided to surgeon 210-1 at user control system 204. To this end, auxiliary system 206 may include a display monitor 214 configured to display one or more user interfaces, such as images (e.g., 2D images) of the surgical area, information associated with patient 208 and/or the surgical procedure, and/or any other visual content as may serve a particular implementation. For example, display monitor 214 may display images of the surgical area together with additional content (e.g., graphical content, contextual information, etc.) concurrently displayed with the images. In some embodiments, display monitor 214 is implemented by a touchscreen display with which surgical team members 210 may interact (e.g., by way of touch gestures) to provide user input to surgical system 200.

While auxiliary system 206 is shown in FIG. 2 as a separate system from manipulating system 202 and user control system 204, auxiliary system 206 may be included in, or may be distributed across, manipulating system 202 and/or user control system 204. Additionally, while user control system 204 has been described as including one or more user input devices and/or audio input devices, other components of surgical system 200 (e.g., manipulating system 202 and/or auxiliary system 206) may include user input devices, audio input devices, and/or audio output devices as may suit a particular implementation.

Manipulating system 202, user control system 204, and auxiliary system 206 may be communicatively coupled one to another in any suitable manner. For example, as shown in FIG. 2, manipulating system 202, user control system 204, and auxiliary system 206 may be communicatively coupled by way of control lines 216, which may represent any optical, wired, or wireless communication link as may serve a particular implementation. To this end, manipulating system 202, user control system 204, and auxiliary system 206 may each include one or more optical, wired, or wireless communication interfaces, such as one or more local area network interfaces, Wi-Fi network interfaces, cellular interfaces, etc.

In some examples, system 100 is implemented entirely by the medical system itself. For example, system 100 may be implemented by one or more computing devices included in surgical system 200 (e.g., in one or more computing devices included within manipulating system 202, user control system 204, and/or auxiliary system 206). In alternative examples, system 100 is implemented entirely by a remote computing system communicatively coupled to the medical system. Alternatively, system 100 may be implemented by (e.g., distributed across) both a medical system and a remote computing system.

Figure 3:
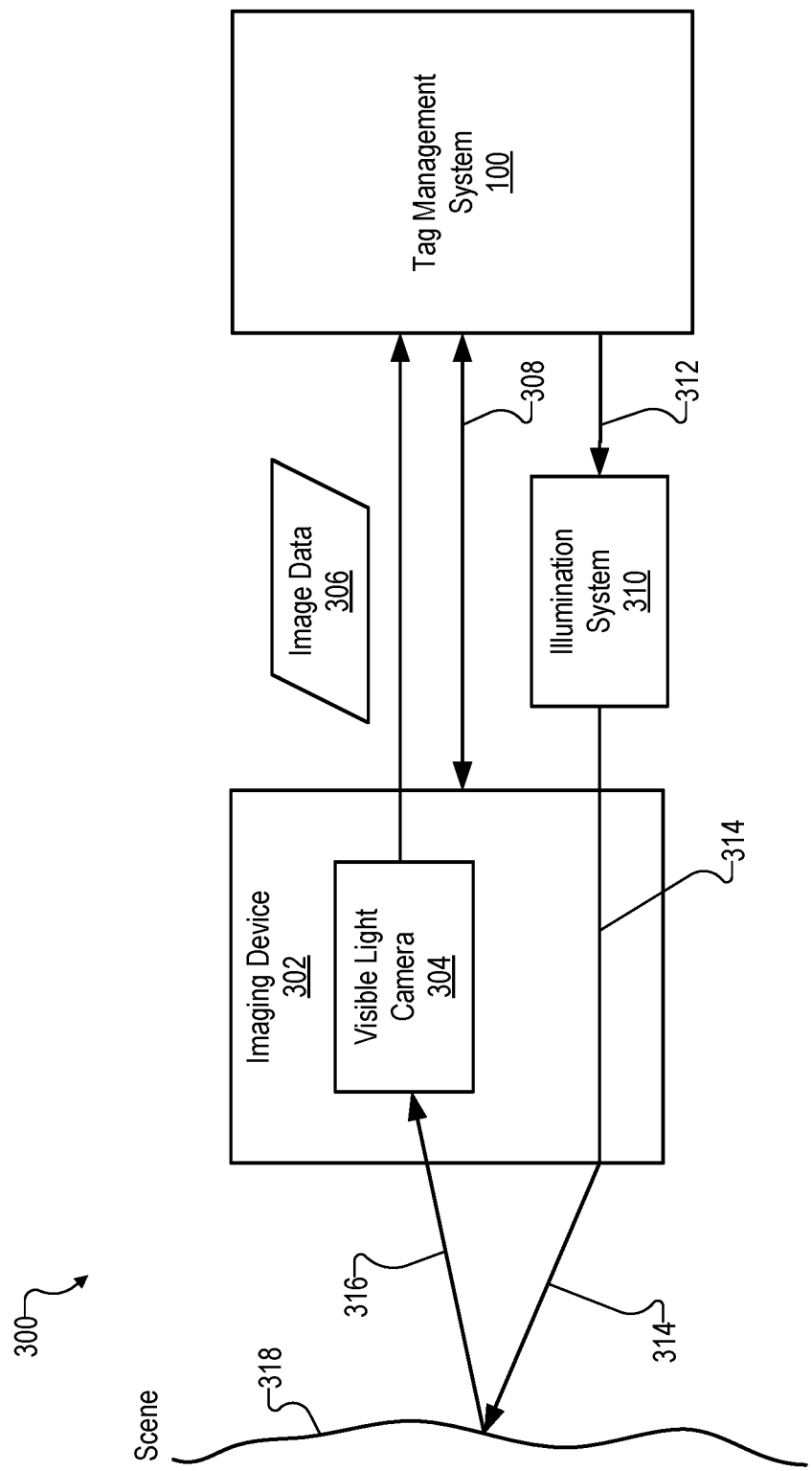
FIG. 3 illustrates an exemplary configuration in which the tag management system of FIG. 1 is communicatively coupled with an exemplary imaging device.

FIG. 3 illustrates an exemplary configuration 300 in which system 100 is communicatively coupled with an exemplary imaging device 302. Imaging device 302 may be used in accordance with the systems and methods described herein to capture visible light images of a region of interest. Imaging device 302 may be implemented by an endoscope or other camera device configured to capture images of the region of interest. In some examples, imaging device 302 may be included in or attached to and controlled by a computer-assisted medical system (e.g., surgical system 200). In alternative examples, imaging device 302 may be hand-held and operated manually by an operator (e.g., a surgeon). In alternative examples, imaging device 302 may be an imaging device that is external to a patient and/or the medical system, such as an operating room camera, a wearable camera (e.g., an augmented reality (AR) or virtual reality (VR) headset), and the like.

As used herein, the "region of interest" refers to any physical location where a medical procedure may be performed, such as a surgical area associated with a patient, an operating room, etc. The region of interest is not limited to the physical location that is within a current field of view of imaging device 302. An image of the region of interest may depict all or a portion of the region interest. For example, for some images of the region of interest the field of view of imaging device 302 captures less than all of the region of interest. For example, when imaging device 302 is implemented by an endoscope, the region of interest may include a surgical area associated with a patient, and images captured by the endoscope may depict all or a portion of the surgical area. In other examples, such as when imaging device 302 is implemented by a camera external to the patient, the region of interest may include the operating room, and images of the region of interest captured by the camera may depict all or a portion of the operating room (e.g., objects external to the patient, such as manipulating system 2020, surgical team members 210, an operating table, etc.).

Imaging device 302 includes a visible light camera 304 ("camera 304") configured to generate and output image data 306. Camera 304 is configured to generate image data 306 representative of an image of a region of interest (e.g., a two-dimensional ("2D") image of the region of interest or a three-dimensional ("3D") image of the region of interest). Camera 304 may be implemented by any one or more suitable image sensors, such as a charge coupled device ("CCD") image sensor, a complementary metal-oxide semiconductor ("CMOS") image sensor, a hyperspectral camera, a multispectral camera, or the like.

System 100 may obtain image data 306 by directing camera 304 to acquire image data 306 and receiving image data 306 from camera 304. To this end, system 100 is communicatively coupled to imaging device 302 by way of a bidirectional communication link 308 and to an illumination system 310 by way of a communication link 312. Communication links 308 and 312 may each be implemented by any suitable wired and/or wireless communication medium as may serve a particular implementation. System 100 may use communication links 308 and 312 to direct camera 304 to acquire image data 306 and receive image data 306, as described herein.

Illumination system 310 may be configured to emit light 314 (e.g., at the direction of system 100) to illuminate the region of interest to be imaged by imaging device 302. The light 314 emitted by illumination system 310 may include visible light and/or non-visible light (e.g., infrared light). As shown, light 314 may travel to the region of interest through imaging device 302 (e.g., by way of an illumination channel within imaging device 302 that may be implemented by one or more optical fibers, light guides, lenses, etc.).

A portion of emitted light 314 (referred to as reflected light 316) may reflect off a surface 318 within the region of interest being imaged by imaging device 302. Surface 318 may represent a surface of a dynamic object located within the region of interest. A dynamic object may be any object that may move (e.g., change its pose) and/or deform (change its shape) within the region of interest. In some examples, such as in cases where imaging device 302 captures a region of interest within an internal space of a patient, a dynamic object may be an endogenous object, such as tissue, blood, an organ, bone, and the like. Additionally or alternatively, a dynamic object may be an exogenous object, such as a surgical instrument, a surgical mesh, a needle, a staple, and the like. In additional examples, such as in cases where imaging device 302 captures images of a region of interest external to a patient, a dynamic object may also include, for example, a person (e.g., patient 208 or a surgical team member 210), a medical system (e.g., surgical system 200) or a component of a medical system (e.g., user control system 204, auxiliary system 206, a manipulator arm 212, an instrument cart, etc.), and any other object that may move or deform within the region of interest.

Camera 304 (and/or other circuitry included in imaging device 302) may generate, based on reflected light 316, image data 306 representative of an image of the region of interest including surface 318. Image data 306 may have any suitable format. Camera 304 may transmit image data 306 to system 100.

As mentioned, in some examples image data 306 may be representative of a 3D image of the region of interest. That is, image data 306 may include right-side image data and left-side image data. Camera 304 may generate a 3D image in any suitable way. In some examples, camera 304 may be configured to capture a 3D image of the region of interest. For example, camera 304 may be implemented by a right-side image sensor configured to capture a right-side perspective image and a left-side image sensor configured to capture a left-side perspective image. Camera 304 (and/or other circuitry included in imaging device 302) may generate right-side image data and left-side image data. In other examples, camera 304 (and/or other circuitry included in imaging device 302) may be configured to generate a 3D image (e.g., right-side image data and left-side image data) of the region of interest based on a captured 2D image and a depth map generated by a depth sensor (not shown) included in imaging device 302.

System 100 may direct display devices to concurrently display the right-side and left-side perspective images in a manner that forms a 3D image of the region of interest. In some examples, the display devices are included in and/or communicatively coupled to a computer-assisted medical system (e.g., surgical system 200).

System 100 may be configured to obtain image data by controlling one or more operations of imaging device 302 and/or illumination system 310. For example, system 100 may direct illumination system 310 to emit light 314 and may activate (e.g., turn on) camera 304. Alternatively, system 100 may obtain image data 306 by receiving raw data from camera 304 and generating image data 306.

Figure 4:
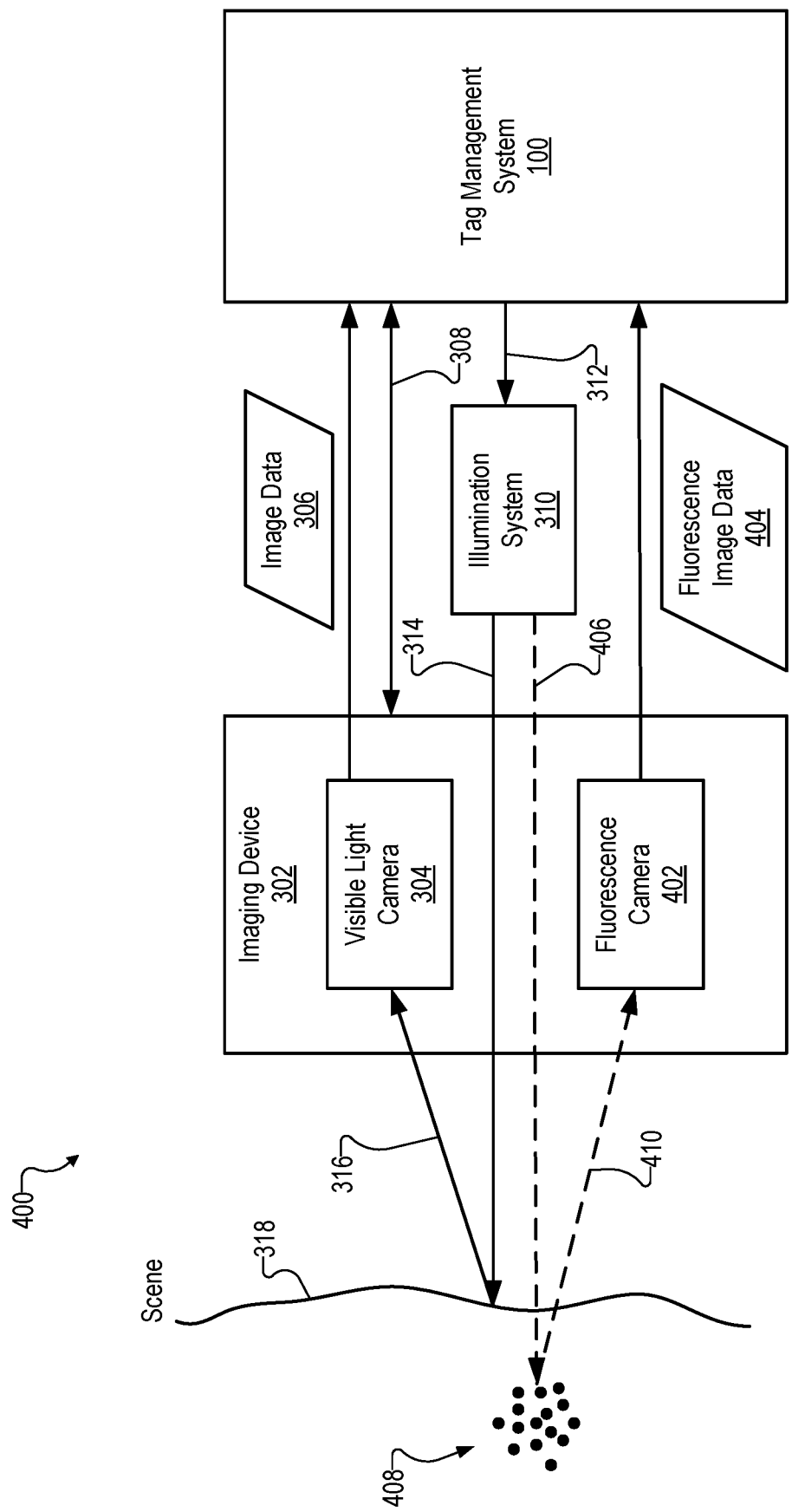
FIG. 4 illustrates another exemplary configuration in which the tag management system of FIG. 1 is communicatively coupled with another exemplary imaging device that includes a fluorescence camera.

Other configurations of imaging device 302 are possible in accordance with the systems and methods described herein. In some examples, imaging device 302 may be configured to generate, in addition to or in place of image data 306, fluorescence image data representative of a fluorescence image of the region of interest. FIG. 4 illustrates an exemplary configuration 400 in which imaging device 302 further includes a fluorescence camera 402 in addition to camera 304.

Fluorescence camera 402 is configured to generate fluorescence image data 404 representative of a fluorescence image of the region of interest. Fluorescence camera 402 may be implemented by any suitable image sensor, such as a CCD image sensor, a CMOS image sensor, a hyperspectral camera, a multispectral camera, or the like. In the example of FIG. 4, fluorescence camera 402 is separate from (i.e., physically distinct from) camera 304. However, in other examples camera 304 and fluorescence camera 402 may be implemented by the same camera.

Illumination system 310 may be configured to emit fluorescence excitation illumination 406 (e.g., at the direction of system 100) to excite a fluorescence imaging agent 408 present at the region of interest. Fluorescence excitation illumination 406 emitted by illumination system 310 may include visible light and/or non-visible light (e.g., infrared light). As shown, fluorescence excitation illumination 406 may travel to the region of interest through imaging device 302 (e.g., by way of an illumination channel within imaging device 302 that may be implemented by one or more optical fibers, light guides, lenses, etc.).

Fluorescence excitation illumination 406 may excite fluorescence imaging agent 408, which emits fluorescence signals 410 while in an excited state. Fluorescence imaging agent 408 may include any fluorophore, dye, protein, or other substance introduced into a body or naturally occurring within the body that emits fluorescence illumination signals 410 when exposed to fluorescence excitation illumination 406. Fluorescence camera 402 may detect fluorescence signals 410 and generate, based on the detected fluorescence signals 410, fluorescence image data 404 representative of a fluorescence image of the region of interest.

In some examples, fluorescence image data 404 may be representative of a 3D fluorescence image of the region of interest. Fluorescence camera 402 may generate a 3D fluorescence image in any suitable way. For example, camera 304 may be configured to capture a 3D fluorescence image of the region of interest. To this end, fluorescence camera 402 may be implemented by a right-eye fluorescence image sensor configured to capture a right-side fluorescence image and a left eye fluorescence image sensor configured to capture a left-side fluorescence image.

System 100 may direct display devices to concurrently display the right-side and left-side fluorescence images in a manner that forms a 3D fluorescence image of the region of interest. In some examples, the display devices are included in and/or communicatively coupled to a computer-assisted medical system (e.g., surgical system 200). In some examples, a fluorescence image may be combined with a visible light image to generate an augmented image. For instance, fluorescing regions included in a fluorescence image may be superimposed on a visible light image to highlight certain anatomical features.

System 100 may be configured to obtain fluorescence image data by controlling one or more operations of imaging device 302 and/or illumination system 310. For example, system 100 may direct illumination system 310 to emit fluorescence excitation illumination 406 and may activate (e.g., turn on) fluorescence camera 402. Thus, system 100 may obtain fluorescence image data 404 by directing fluorescence camera 402 to acquire fluorescence image data 404 and receiving fluorescence image data 404 from fluorescence camera 402. Alternatively, system 100 may obtain fluorescence image data by receiving raw data from fluorescence camera 402 and generating fluorescence image data 404.

Figure 5:
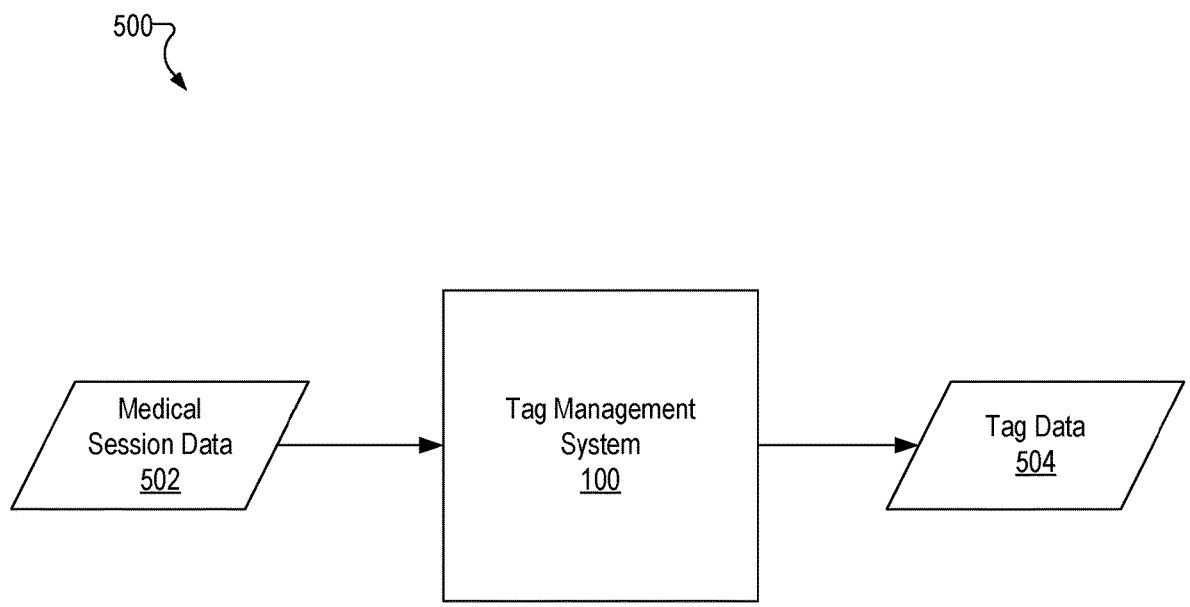
FIG. 5 illustrates an exemplary configuration in which the tag management system of FIG. 1 may generate, based on medical session data, a tag associated with an event that occurs within a region of interest during a medical session.

As will now be explained, system 100 may be configured to render, within an image captured by an imaging device (e.g., imaging device 302), a graphical tag representative of an event that occurs within a region of interest and/or adjust a pose of an instrument (e.g., a surgical instrument located within the region of interest) based on a physical location within the region of interest and that is associated with a graphical tag element representative of an event that occurs within the region of interest. FIG. 5 illustrates an exemplary configuration 500 in which system 100 may generate, based on medical session data 502, tag data representative 504 of a tag associated with an event that occurs within a region of interest during a medical session. A tag is a set of information that may provide context regarding a particular event, such as an identification and/or description of the event, a physical location within the region of interest where the event occurred, a timestamp indicating when the event occurred, a user associated with the event, and/or content associated with the event (e.g., image and/or video content that depicts the occurrence of the event, a 3D model of the physical location of the event, etc.).

As shown, system 100 may access medical session data 502 associated with and/or generated during a medical session performed with a computer-assisted medical system (e.g., surgical system 200). Medical session data 502 accessed by system 100 may be generated during the medical session and may be based on one or more operations performed by the computer-assisted medical system during the medical session. The operations performed by the computer-assisted medical system may include any mechanical, electrical, hardware, and/or software-based operations as may serve a particular implementation. The medical session data may be generated by the computer-assisted medical system, by one or more components coupled to the computer-assisted medical system during the medical session (e.g., one or more medical instruments), by a user device communicatively paired with the computer-assisted medical system during the medical session, and/or by any other device associated with the computer-assisted medical system as may serve a particular implementation. Medical session data may include, for example, kinematic data, image data, sensor data, instrument data, and/or any other type of data as may serve a particular implementation. In some examples, medical session data 502 includes surgical session data generated during a surgical session and based on one or more operations performed by a computer-assisted surgical system (e.g., surgical system 200).

Kinematic data may be representative of a pose (e.g., a position and/or an orientation) of a component within the computer-assisted medical system and/or a component coupled to the computer-assisted medical system. For example, kinematic data may be representative of a pose of a manipulator arm 212 and/or a surgical instrument coupled to a manipulator arm 212 of surgical system 200.

Image data may be representative of one or more images captured by an imaging device coupled to the computer-assisted medical system. For example, image data may be representative of one or more images captured by imaging device 302 (e.g., a stereoscopic endoscope coupled to a manipulator arm 212 of surgical system 200). The one or more images may constitute one or more still images and/or video streams captured by the imaging device. In some examples, system 100 may access image data by receiving (e.g., by way of a network) images output by the imaging device.

Sensor data may include any data generated by sensors included in or associated with a computer-assisted medical system (e.g., surgical system 200). Sensor data may be representative of any sensed parameter as may serve a particular implementation. For example, sensor data may be indicative of motion of a surgical instrument.

Instrument data may include any data generated by a medical instrument (e.g., a surgical instrument), and may be representative of an identification ("ID") of the instrument, an operational state of the instrument (e.g., open, closed, electrically charged, idle, etc.), a fault code of the instrument, and any other information associated with an instrument.

A medical session may be any session during which manual and/or instrumental techniques are used to investigate, diagnose, and/or treat a physical condition of a patient. Additionally or alternatively, a medical session may include non-clinical procedures, e.g., procedures that are not performed on a live patient, such as calibration or testing procedures, training procedures, experimental or research procedures, and the like. A medical session may also include any associated preparatory and concluding procedures, activities, and/or operations.

System 100 may determine, based on medical session data 502, that an event occurs within a region of interest and generate, based on medical session data 502, tag data 504 representative of a tag associated with the event. Tag data 504 may include any suitable data in any suitable format as may serve a particular implementation. System 100 may use tag data 504 to provide information and/or content about the event and/or to control operations of the medical system (e.g., control operation of a surgical instrument coupled to a manipulator arm 212).

For example, tag data 504 may include graphical tag data representative of a graphical tag to be rendered, within an image of a region of interest, at an image location that depicts a physical location on a surface of a dynamic object. System 100 may use the graphical tag data to render, within an image of the region of interest and at an image location that depicts a physical location on a surface of a dynamic object, a graphical tag representative of an event that occurred within the region of interest.

A graphical tag as used herein is a graphical element, such as a shape, an icon, text, false coloring, etc., that may be rendered within an image of a region of interest and that represents an event that occurred within the region of interest. By rendering the graphical tag within an image of a region of interest at an image location that depicts a physical location on a surface of a dynamic object, the graphical tag has spatial memory. That is, in one or more subsequently captured images the graphical tag remains in place with the dynamic object even when the dynamic object moves or deforms within the region of interest. Thus, a user may refer to the graphical tag to identify a physical location within the region of interest where an event occurred, even if objects within the region of interest have moved or deformed.

Exemplary systems and methods by which system 100 may generate tag data 504 and render the graphical tag will now be described. For ease of discussion, the exemplary systems and methods will be described with reference to a surgical session performed with a computer-assisted surgical system (e.g., surgical system 200). However, the systems and methods may be applied to any type of medical session performed with any suitable type of medical system (e.g., a computer-assisted medical system).

System 100 may access surgical session data for a surgical session performed with a computer-assisted surgical system (e.g., surgical system 200) and, based on the surgical session data, determine that an event occurs within a region of interest associated with the surgical session. In some examples, the event occurs within a field of view of an imaging device. In alternative examples, the event occurs outside the field of view of the imaging device.

In some examples, surgical session data accessed by system 100 may be generated during the surgical session and may be based on one or more operations performed by the computer-assisted surgical system during the surgical session. Surgical session data generated during a surgical session may include various types of data. For example, surgical session data generated during a surgical session may include kinematic data, image data, depth data, sensor data, surgical instrument data, and/or any other type of data as may serve a particular implementation.

In some examples, system 100 may additionally or alternatively access surgical session data generated by the computer-assisted surgical system during one or more other surgical sessions that, for example, precede the current surgical session. For example, system 100 may obtain surgical session data during a first surgical session in which the computer-assisted surgical system is used to perform a first surgical procedure with respect to a first patient. System 100 may also obtain additional surgical session data during a second surgical session in which the computer-assisted surgical system is used to perform a second surgical procedure with respect to the patient or another patient. During the second surgical session, system 100 may access both the surgical session data and the additional surgical session data. Surgical session data that is generated prior to a current surgical session may be referred to herein as "historical surgical session data." As will be described below, historical surgical session data may allow system 100 to more effectively identify and/or predict an event that may occur during the second surgical session.

System 100 may additionally or alternatively access surgical session data based on operations performed by one or more computer-assisted surgical systems other than the computer-assisted surgical system being used during a particular surgical session. For example, system 100 may access surgical session data generated during a plurality of distinct computer-assisted surgical sessions located within a particular medical center, a network of hospitals, and/or any other grouping. This type of surgical session data may be referred to herein as "global surgical session data" and, as will be described below, may allow system 100 to more effectively identify and/or predict an event that may occur during a particular surgical session in which a particular computer-assisted surgical system included in the grouping is used to perform a surgical procedure.

In some examples, system 100 may provide a user interface configured to allow a user to define a particular grouping of computer-assisted surgical sessions and/or computer-assisted surgical systems from which surgical session data may be accessed by system 100.

System 100 may determine, based on surgical session data for the surgical session, historical surgical session data, and/or global surgical session data (referred to collectively as "surgical session data"), that an event occurs during the surgical session within a region of interest associated with the surgical session (e.g., within a surgical area internal to a patient, within an operating room, etc.).

An event may occur during a preoperative phase, an operative phase, and/or a postoperative phase of a surgical session. Exemplary preoperative phase events may include, but are not limited to, setup of surgical system 200, attaching surgical instruments to manipulator arms 212, draping surgical system 200, preparing a patient for the surgical procedure (e.g., bringing the patient into the operating room, checking patient vital signs, providing intravenous fluids, administering anesthesia to the patient), and positioning and/or targeting surgical system 200 with respect to the patient.

Exemplary operative phase events may include, but are not limited to, opening a surgical area associated with a patient (e.g., by making an incision on external patient tissue), inserting a surgical instrument into the patient, performing surgical operations on patient tissue (e.g., by cutting tissue, repairing tissue, suturing tissue, cauterizing tissue, etc.), closing the surgical area associated with the patient (e.g., removing surgical instruments from the patient, closing/suturing the incision point, dressing any wounds, etc.), and detecting contact of an endoscope tip with tissue.

Exemplary postoperative phase events may include, but are not limited to, removing surgical system 200 from the patient, patient care and recovery operations (e.g., removing the patient from the operating room, monitoring the patient as the patient recovers from the surgical procedure, etc.), cleaning the operating room, cleaning and/or sterilizing surgical system 200 and/or surgical instruments used during the surgical session, receiving reporting documentation by surgical team members, and patient discharge operations.

System 100 may determine that an event occurs in any suitable way. In some examples, the computer-assisted surgical system may log events as they occur, and system 100 may access the system log to determine that an event occurs. For example, surgical system 200 may log each firing/activation of a stapler instrument, each instance of energization of a cauterization instrument, each collision of manipulator arms 212 and/or surgical instruments, and any other event logged or tracked by the computer-assisted surgical system.

As another example, a user may manually place a fiducial marker at a desired location, which may be logged by the surgical system as a fiducial marking event. For example, a user may provide user input (e.g., by manipulation of a user input device included in user control system 204) to draw one or more fiducial markers on an image of the region of interest. Fiducial markers may be similar to a graphical tags and may be used for various purposes such as marking a location of interest, guiding an excision, suturing process, and/or any other procedure.

Figure 6:
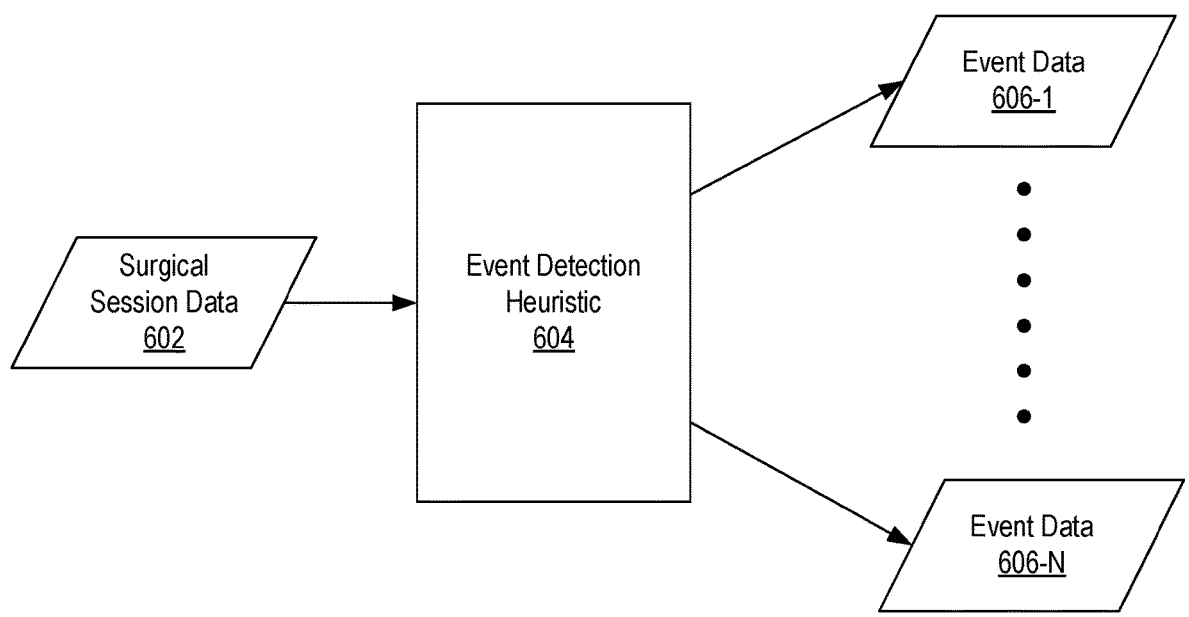
FIG. 6 illustrates an exemplary manner in which the tag management system may infer the occurrence of an event based on surgical session data.

In additional or alternative examples, system 100 may infer, based on an analysis of surgical session data, that an event occurs. FIG. 6 illustrates an exemplary manner in which system 100 may infer the occurrence of an event based on surgical session data. As shown, system 100 may apply surgical session data 602 as an input to an event detection heuristic 604. Event detection heuristic 604 may analyze the surgical session data 602 and output various instances of event data 606 (e.g., event data 606-1 through event data 606-N). Each instance of event data 606 may represent a particular event identified by event detection heuristic 604.

Event detection heuristic 604 may include any suitable heuristic, process, and/or operation that may be performed or executed by system 100 and that may be configured to identify events based on surgical session data 602. To illustrate, event detection heuristic 604 may detect an indicator and/or pattern in surgical session data that is indicative of an occurrence of a particular event.

For example, kinematic data generated during a particular portion of a surgical session may indicate movement of a surgical instrument in a suturing pattern. Additionally, surgical instrument data may indicate that the surgical instrument used during the same portion of the surgical session is a needle driver. Based on this kinematic data and surgical instrument data, system 100 may determine that a suturing event is occurring or has occurred.

In some examples, surgical session data 602 may include historical surgical session data, as described above. In these examples, one of the instances of event data 606 output by event detection heuristic 604 may be representative of an event that system 100 predicts will occur based on the historical surgical session data. For example, the historical surgical session data may include surgical session data generated during multiple surgical sessions in which the same type of surgical procedure is performed with the computer-assisted surgical system. Based on this historical surgical session data, event detection heuristic 604 may predict that a certain second event will occur following the occurrence of a certain first event.

In some examples, surgical session data 602 may include global surgical session data, as described above. In these examples, one of the instances of event data 606 output by event detection heuristic 604 may be representative of an event that is determined to occur based on the global surgical session data. For example, the global surgical session data may indicate that a particular kinematic data value for a particular surgical tool indicates that the surgical tool is located within a predetermined distance from another surgical tool. When the actual kinematic data for the surgical tool being used during the surgical session is equal to or less than this value, event detection heuristic 604 may detect an event that indicates that the surgical tool has moved to a location within the predetermined distance from the other surgical tool.

Event detection heuristic 604 may receive additional or alternative types of input as may serve a particular implementation. For example, event detection heuristic 604 may accept user profile data (e.g., data representative of a user profile of one or more surgical team members involved with a surgical session) as an additional input. In this configuration, event detection heuristic 604 may detect events based on both surgical session data 602 and the user profile data.

To illustrate, the user profile data may include data representative of a user profile of a surgeon involved with a surgical session. The user profile for the surgeon, combined with the surgical session data, may indicate that the surgeon performs various operations in a certain order unique to the surgeon. Accordingly, event detection heuristic 604 may detect that a particular event is going to occur in accordance with the certain order.

Event detection heuristic 604 may additionally or alternatively accept user input data as an additional input. User input data may be representative of information input by a user by way of a computing device included in the computer-assisted surgical system or communicatively paired with the computer-assisted surgical system. In this configuration, event detection heuristic 604 may detect events based on both surgical session data 602 and the user input data. The user input data may include, for example, information input by way of an application executed by a user device associated with a surgical team member.

To illustrate, a user (e.g., an anesthesiologist) may input, via an application currently being executed by a user device communicatively paired with a computer-assisted surgical system, information indicating that a patient is fully sedated. This information, combined with the surgical session data, may indicate that a preoperative phase of the surgical session has ended. Accordingly, event detection heuristic 604 may detect that a particular event is likely to occur, such as opening of an incision site on the patient.

In some examples, event detection heuristic 604 may implement a machine learning model. The machine learning model may use historical surgical session data, global surgical session data, user profile data, user input data, or any combination or sub-combination thereof, to identify one or more unique patterns of surgical system operations and associate events with the detected patterns of surgical system operations. As system 100 collects more data, event data 606 output by event detection heuristic 604 may be updated or corrected, as necessary.

In response to determining that an event occurs within a region of interest associated with a surgical session, system 100 may identify a physical location within the region of interest and that is associated with the event (the "event location"). In some examples, the event location is a location on a surface of a dynamic object (e.g., an organ) located within the region of interest. In additional or alternative examples, the physical location is a 3D position within a reference 3D coordinate system of the computer-assisted surgical system and/or imaging device.

The physical location may be associated with the event in any suitable way. For example, a physical location associated with an event that occurs at or near a particular location on a surface of a dynamic object located within the region of interest is the location on the surface of the dynamic object. To illustrate, a physical location associated with a suturing event or a cauterization event may be a location on the surface of tissue where the tissue is sutured or cauterized. As another illustration, a physical location associated with a docking event may (e.g., docking of a surgical instrument to a manipulator arm 112) may be an interface between the surgical instrument and the manipulator arm 112. As another illustration, a physical location associated with a draping event may be a surface of a manipulator arm 112 that is draped.

In other examples in which an event includes an operation or action performed by a dynamic object (e.g., a surgical instrument) located within the region of interest, the physical location may be a location on a surface of the dynamic object that performs the event, or a location (e.g., a 3D position) of the dynamic object within the region of interest when the dynamic object performs the event. To illustrate, a physical location associated with a needle drop event (e.g., when a needle driver drops a needle) may be a distal end of the needle driver. Alternatively, the physical location associated with the needle drop event may be a 3D location, within the region of interest, of the distal end of the needle driver when the needle driver dropped the needle.

System 100 may identify the event location in any suitable way. In some examples, system 100 may identify the event location (e.g., a physical location on a surface of a dynamic object) based on image data, such as by image segmentation. In other examples, system 100 may identify the event location (e.g., a 3D position within the region of interest) based on kinematic data, surgical instrument data, depth data, and/or any other surgical session data as may suit a particular implementation. Methods of identifying the event location are described below in more detail.

In some examples, system 100 may identify, in response to identifying the event location, an image location at which a graphical tag representative of the event may be rendered. The image location is a location within an image of the region of interest (e.g., a visible light image) captured by an imaging device (e.g., imaging device 302). System 100 may then render, within the image at the identified image location, the graphical tag.

As used herein, an image location may be any pixel or group of pixels within the image (e.g., an m×n region of pixels, a group of pixels of a particular object included within the image, etc.) that depicts the event location.

System 100 may identify the image location in any suitable way. In some examples, system 100 may identify the image location within an image (e.g., a 2D image or a 3D image) based on image data. For example, system 100 may receive, from an image device, a plurality of images (e.g., a visible light image stream). System 100 may segment one or more of the images, such as by classifying different portions of the images as corresponding to different objects (e.g., types of tissue, organs, surgical instruments, and/or any other objects). In some examples, system 100 may segment the images by applying the image data, and optionally any other suitable surgical session data, to a classification heuristic and performing the classification heuristic to identify objects within the image. In another example, system 100 may identify objects within the image by inputting the image data, and any other suitable surgical session data, into a machine learning model configured to identify image features. The machine learning model may be trained and/or used in any suitable manner. System 100 may determine, based on one or more objects identified within one or more images of the region of interest, that an event occurs within the region of interest. For example, system 100 may determine that an event occurs based on the presence or absence of a particular object, based on characteristics of a particular object (e.g., shape, color, brightness, etc.), and/or based on a change detected in a particular object.

In response to a detection that an event occurs, system 100 may designate one of the image objects used in the event detection as an image object representative of the event location ("designated image object"). In some examples, system 100 may store data representative of the designated image object as tag data (e.g., tag data 504) associated with the event. System 100 may render, within the image of the region of interest, a graphical tag at an image location of the designated image object, e.g., at an image location that depicts the event location (e.g., a location on a surface of a dynamic object located within the region of interest).

In the examples just described, the image in which the graphical tag is rendered is an initial image captured when system 100 determines that the event occurs. That is, the initial image includes the image object that triggered the determination that the event occurs. Thus, the graphical tag may be rendered nearly instantaneously (e.g., in real-time) with the occurrence of the event. It will be understood, however, that the processing described above may also be performed at a later time, such as during playback of the image stream.

The graphical tag may additionally or alternatively be rendered within a subsequently captured image (e.g., an image captured after the event occurs or captured after the initial image). To this end, system 100 may segment the subsequently captured image to identify and/or classify one or more objects within the subsequently captured image. The subsequently captured image may be segmented in any suitable way, including any method described herein. System 100 may then identify an object in the subsequently captured image that matches or corresponds to the tag data associated with the event (e.g., data representative of the designated image object). System 100 may identify, within the subsequently-captured image, an image location of the matching/corresponding object and render the graphical tag at the identified image location. Thus, the graphical tag may be rendered, within the subsequently-captured image, at an image location that depicts the event location. This process for rendering the graphical tag within a subsequently captured image may be repeated for each subsequently captured image included in a stream of images (e.g., a video stream) of the region of interest.

By rendering the graphical tag at an image location of the designated image object, the graphical tag moves with the object as the object changes position and/or form within the region of interest. Thus, the graphical tag has spatial memory. Exemplary configurations and manners of rendering and using a graphical tag will be described in more detail below.

Figure 7:
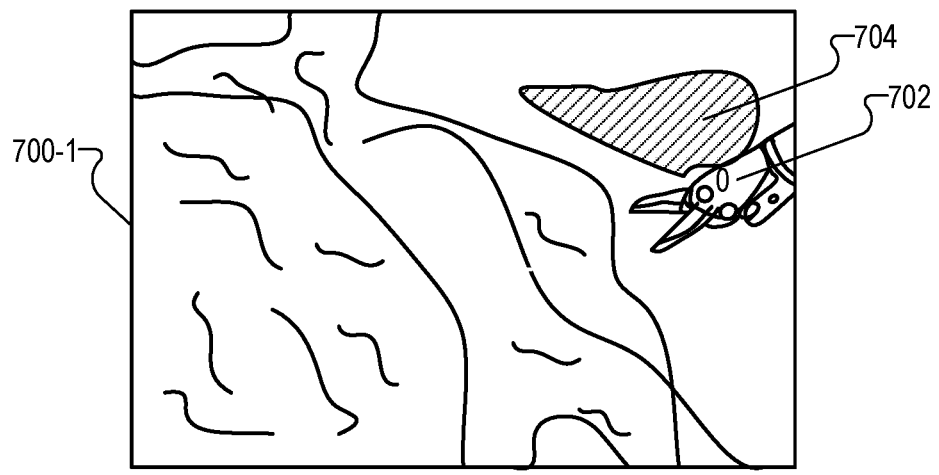
FIG. 7 illustrates exemplary images that the tag management system may use to identify an image location at which a graphical tag may be rendered.
Figure 7:
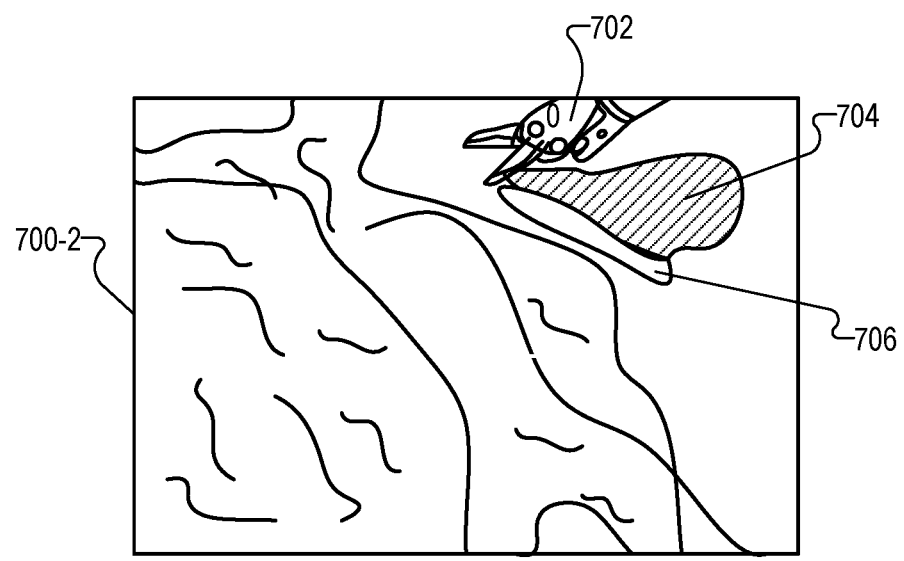
Figure 8:
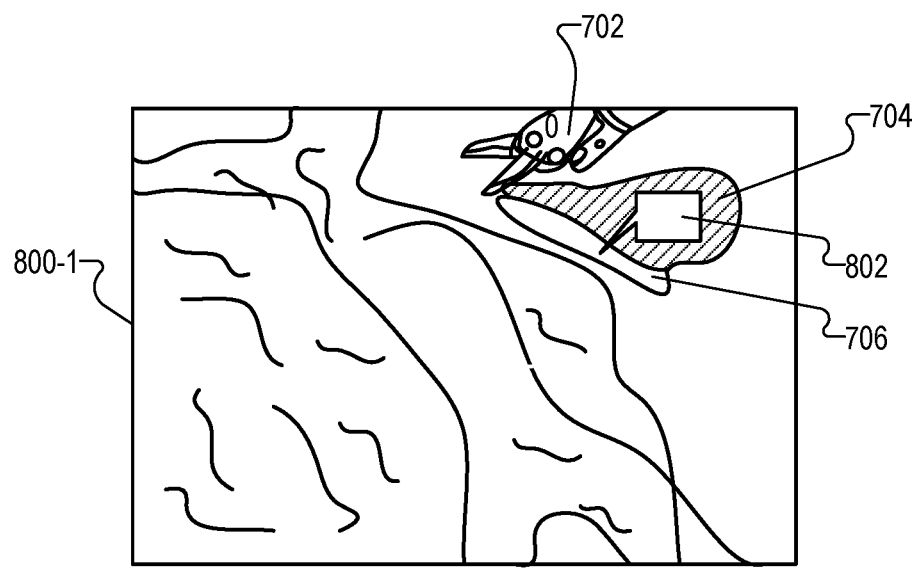
FIG. 8 illustrates exemplary images in which a graphical tag associated with an event is rendered.
Figure 8:
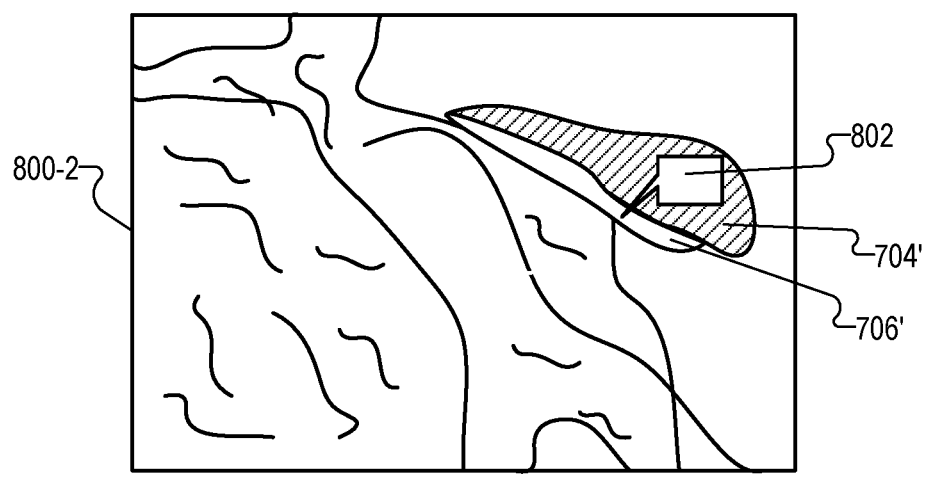

The preceding examples will be illustrated with reference to FIGS. 7 and 8. FIG. 7 illustrates exemplary images 700-1 and 700-2 that system 100 may use to identify an image location at which a graphical tag is to be rendered. FIG. 8 illustrates exemplary images 800-1 and 800-2 in which a graphical tag associated with an event is rendered. Referring now to FIG. 7, image 700-1 may be captured by an imaging device (e.g., imaging device 302) aimed at an internal space of a patient, and may be represented by image data (e.g., image data 306). Image 700-2 may be captured by the imaging device subsequently to capture of image 700-1 and may also be represented by the image data. Image 700-1 depicts a surgical instrument 702 (e.g., a cutting tool), which is about to perform a cutting operation with respect to a tissue defect 704. As shown in image 700-2, surgical instrument 702 has completed the cutting operation, and thus also depicts a cut region 706. System 100 may segment image 700-1 and image 700-2 and determine, based on the presence of cut region 706 in only image 700-2 (and optionally also based on a detection of surgical instrument 702 near cut region 706), that a cutting event has occurred.

Referring now to FIG. 8, image 800-1 may be captured by the imaging device. Image 800-1 is the same as image 700-2 except that a graphical tag 802 representative of the cutting event is rendered within image 800-1. To this end, system 100 may designate cut region 706 as the designated image object (the image object representative of the cutting event location) and store data representative of cut region 706 as tag data associated with the cutting event. System 100 may then render graphical tag 802 within image 800-1 at an image location of cut region 706.

Image 800-2 may be captured by the imaging device subsequently to the cutting event (and subsequently to capture of image 800-1). As shown in image 800-2, tissue defect 704' and cut region 706' have deformed and moved within the region of interest so that they are not at the same position as when image 800-1 was captured (even though the imaging device has not moved within the region of interest). Nevertheless, system 100 may segment image 800-2 and determine that cut region 706' best matches the stored tag data representative of the designated image object (i.e., cut region 706). Accordingly, system 100 may render graphical tag 802 at a new image location of cut region 706'.

In some examples, system 100 may additionally or alternatively identify the image location based on a 3D position, within the reference 3D coordinate system, associated with the event. This method may be used, for example, when system 100 detects occurrence of the event based on information other than, or in addition to, image data. For example, in response to a determination that an event occurs, system 100 may determine a 3D position associated with the event (the "3D event position").

In some examples, the 3D event position is a location on a surface of a dynamic object (e.g., a surgical instrument), and the image location at which the graphical tag may be rendered is a location, within an image, that depicts a surface of a dynamic object within the region of interest. To accomplish this, system 100 may identify a corresponding location, within an image (e.g., a 2D image or a 3D image), that depicts the 3D event position. System 100 may identify the location that depicts the 3D event position in any suitable way. For example, when the imaging device is registered to the reference 3D coordinate system of the computer-assisted surgical system (e.g., when a position and orientation of the imaging device within the reference 3D coordinate system are known), system 100 may determine the corresponding location, within the image, that depicts the 3D event position. In some examples, system 100 may also use a depth map of the region of interest to determine the image location, within the image, that depicts the 3D event position.

System 100 may segment the image to identify and/or classify one or more objects within the image. The image may be segmented in any suitable way, including any method described herein. System 100 may identify an object that is located at the image location that depicts the 3D event position and designate such image object as the designated image object (i.e., the image object representative of the event location). System 100 may store data representative of the designated image object with tag data associated with the event. System 100 may then render, within the image, a graphical tag at an image location of the designated image object.

System 100 may also render the graphical tag within one or more subsequently captured images in the same or a similar manner as described above with reference to image 700-2.

When the graphical tag is to be rendered within a 3D image and the imaging device is registered with the reference 3D coordinate system, system 100 may omit the step of identifying the corresponding location, within the 3D image, that depicts the 3D event position. Rather, in response to determining the 3D event position, system 100 may segment the 3D image and identify an image object that is located at the 3D event position. In some examples system 100 may use a depth map to segment the 3D image and identify an image object that is located at the 3D event position. System 100 may then designate such image object as the designated image object representative of the event location.

In some examples, system 100 may use a depth map to determine a 3D position of the physical location on the surface of the dynamic object. The graphical tag may then be rendered within the 3D image at the 3D position of the physical location on the surface of the dynamic object. In this way the graphical tag appears to be in physical contact with the physical location on the surface of the dynamic object.

In the examples just described, system 100 uses the 3D event position to determine the designated image object. System 100 may then render, within an image, a graphical tag at an image location of the designated image object.

Figure 9:
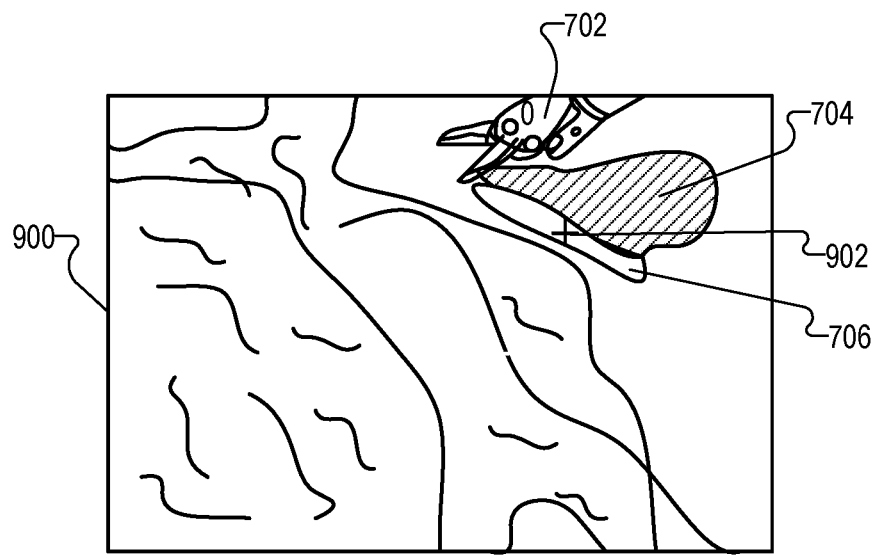
FIG. 9 illustrates an exemplary image that may be used by the tag management system to identify an image location at which a graphical tag may be rendered.

The preceding examples based on using 3D event position data will now be illustrated with reference to FIGS. 7-9. Referring now to FIG. 7, system 100 may determine that a cutting event occurs. This may be determined based on image data as explained above, or it may additionally or alternatively be based on surgical instrument data and/or kinematic data (e.g., data indicating repeated opening and closing of the scissors of surgical instrument 702 and/or movement of surgical instrument 702). In response, system 100 may determine a 3D position of surgical instrument 702 based on kinematic data associated with surgical instrument 702. The kinematic data may specify, for example, a 3D position, within a reference 3D coordinate system, of the distal end of surgical instrument 702 (e.g., the tip of the scissors) when the event begins (e.g., when operation of the scissors begins), when the event ends (e.g., when operation of the scissors ends), or at any time in between (e.g., a midpoint of the event duration, a midpoint of the total distance traversed by surgical instrument 702, an average position for the event duration, etc.).

System 100 may then identify a location, within image 700-2, that depicts the 3D event position. FIG. 9 illustrates an exemplary image 900 that may be used by system 100 to identify an image location at which a graphical tag is to be rendered. Image 900 is the same as image 700-2 except that an image location that depicts the 3D event position is indicated by cross-hairs 902. System 100 may segment image 900 and identify various image objects, including cut region 706, included in image 900. System 100 may determine that cut region 706 corresponds to cross-hairs 902 and thus designate cut region 706 as the designated image object representative of the event location. System 100 may store data representative of cut region 706 as tag data associated with the cutting event. System 100 may then render, within image 800-1 (see FIG. 8), graphical tag 802 at an image location of the designated image object (i.e., cut region 706).

System 100 may also render graphical tag 802 in subsequently captured image 800-2. For example, system 100 may segment image 800-2 and determine that cut region 706' matches the stored tag data representative of the designated image object (i.e., cut region 706). Accordingly, system 100 may render graphical tag 802 at the new image location of cut region 706.

Although graphical tag 802 is shown in FIG. 8 to be in the form of a bubble-type graphical element, any other suitable graphic indication may be used to represent the graphical tag, including but not limited to highlighting the designated image object, shading the designated image object with color, outlining the designated object, and/or any other suitable graphic indication.

In some examples, the image location at which the graphical tag may be rendered is a location, within an image (e.g., image 800-1 or 800-2), that depicts the 3D event position. For example, the event location may not be on the surface of a dynamic object (e.g., a needle drop event may occur above the surface of tissue). Accordingly, system 100 may simply render the graphical tag at an image location that depicts the 3D event position. Such graphical tag may also be rendered in subsequently captured images at the same 3D event position, regardless of how dynamic objects may move or deform within the region of interest.

In the examples described above, tag data associated with a detected event (e.g., tag data 504) may include data representative of the designated image object and/or data representative of the 3D event position. The tag data associated with the event may include any additional or alternative data as may suit a particular implementation. In some examples, the tag data associated with the event may include timestamp data indicating when the event occurred, user data associated with the event (e.g., a user identification associated with the event), and/or any other suitable data as may serve a particular implementation.

In the examples described above, system 100 may render a graphical tag associated with the event. In alternative embodiments, rendering of the graphical tag is optional. For example, system 100 may not render a graphical tag associated with the event but may instead store the identified event location information as tag data associated with the event.

In some examples, system 100 may be configured to identify content associated with the event and/or event location and associate the content with the event location and/or graphical tag (e.g., store the content, an identification of the content, and/or a link to the content as tag data representative of the event). System 100 may then provide, after the event occurs, a user with access to the content based on proximity of an instrument to the event location, as will be described in more detail further below.

The content may include, for example, one or more images (e.g., a video clip, a fluorescence image, etc.) depicting the physical location when the event occurred (e.g., one or more images captured when the event occurred), one or more images captured from a prior medical session, an instructional video (e.g., a tutorial, a diagrammed procedure, etc.). Additionally or alternatively, the content may include text information, such as an event description, user-provided information (e.g., annotation, notes, etc.), a message, and the like. Additionally or alternatively, the content may include audio content, such as audio content recorded when the event occurs, audio content recorded from a prior medical session, instructional audio content (e.g., a tutorial), user-provided audio content (e.g., voiced annotations), and any other suitable audio content. Additionally or alternatively, the content may include content (e.g., images, a 3D model, etc.) from a preoperative image source, such as from a computer-aided tomography (CT) scanner, a magnetic resonance imaging (MRI) device, an ultrasound device, a three-dimensional scanning (LIDAR) device, and/or any other suitable alternative imaging device configured to generate a preoperative image of the patient.

In some examples, system 100 may identify the content based on a user profile of a user (e.g., surgeon 210-1, a user logged into a control system the computer-assisted surgical system, etc.) of the surgical system. For example, system 100 may determine, based on user preferences, that the user prefers certain type of content (e.g., instructional content, 3D model content, video content, still-image content, content associated with particular event types (e.g., error events or tissue-interaction events), etc.) and/or content from a particular source (e.g., a particular medical facility, a particular surgeon, a particular expert) and associate such content with the tag. System 100 may also identify historical content associated with the user (e.g., recorded content from a prior surgical session performed by the user). System 100 may additionally or alternatively identify the content based on surgical session data and/or event data, such as procedure type, patient type, event type, and/or any other information.

In some examples, the content associated with the event location and/or tag may be a fluorescence image captured when a fluorescence event occurs. The intensity of fluorescence signals are initially weak after administration of a fluorescence imaging agent to a patient. As the intensity of the fluorescence signals increases over time the contrast level of the fluorescence image increases until it reaches an optimum range where the fluorescence signals provide useful information about the region of interest (e.g., distinguish different features within the region of interest). As the fluorescence signals continue to increase and the fluorescence image becomes saturated with fluorescence signals the contrast decreases. Accordingly, there is a relatively small window of time during which a fluorescence image may be useful (e.g., during which the contrast level is considered optimum).

To enable use of the fluorescence image outside of the narrow window of time, system 100 may identify a fluorescence image having a contrast level within the optimum range and associate the fluorescence image with the graphical tag. The graphical tag may enable a user to access and view the fluorescence image at a later time, as will be described later in more detail.

System 100 may receive a fluorescence image stream (e.g., fluorescence image data 404 over time) and determine, based on the fluorescence image stream, that a fluorescence event occurs. A fluorescence event occurs when system 100 determines that a contrast level of a fluorescence image included in the fluorescence image stream is within a predefined range (e.g., greater than or equal to a minimum contrast threshold level but less than a maximum contrast threshold level). The predefined range may be empirically set, and in some examples may be set based on particular anatomy to be imaged. For example, tissue that has dense vasculature may have a lower predefined range (or at least a lower maximum threshold level) than tissue with less dense vasculature.

The contrast level of the fluorescence image may be measured in any suitable way. In some examples, the contrast level is measured based on the quantity, density, and/or shape of features and/or structures of fluorescence signals. For example, system 100 may measure contrast by comparing the quantity of linear fluorescing regions (representative of vasculature) within a fluorescence image with a grayscale (or black) image of the region of interest that has little or no fluorescing regions.

In some examples, system 100 may measure the contrast of sub-regions of the fluorescence image. The sub-regions of the fluorescence image may be blocks of pixels (e.g., m×n blocks of pixels) or groups of pixels corresponding to segmented image objects identified in a visible light image captured simultaneously with the fluorescence image. Different sub-regions of the fluorescence image may reach the predefined range at different times depending on the anatomy depicted by the sub-regions. System 100 may determine that the contrast level of the fluorescence image is within the predefined range in any suitable way, such as when at least one sub-region is within the predefined range, when all sub-regions are within the predefined range, when a predefined number of regions are within the predefined range, or when an average contrast of all sub-regions is within the predefined range.

When system 100 determines that the contrast level of the fluorescence image reaches a predefined range (a fluorescence event), system 100 may generate, in response to detection of a fluorescence event, a tag representative of the fluorescence event. For example, system 100 may identify a physical location within the region of interest and associated with the fluorescence event (the "fluorescence event location") and store the fluorescence event location as tag data. The physical location may be associated with the fluorescence event in any suitable way. In some examples, the fluorescence event location is a 3D pose of the imaging device within the region of interest when the fluorescence event occurs. In additional or alternative examples, the fluorescence event location is a physical location on a surface of an object (e.g., a dynamic object) from which the fluorescence signals that are within the optimum range originate.

System 100 may also render, within a visible light image of the region of interest, a graphical tag representative of the fluorescence event. The graphical tag may be rendered at an image location that depicts the fluorescence event location.

Figure 10:
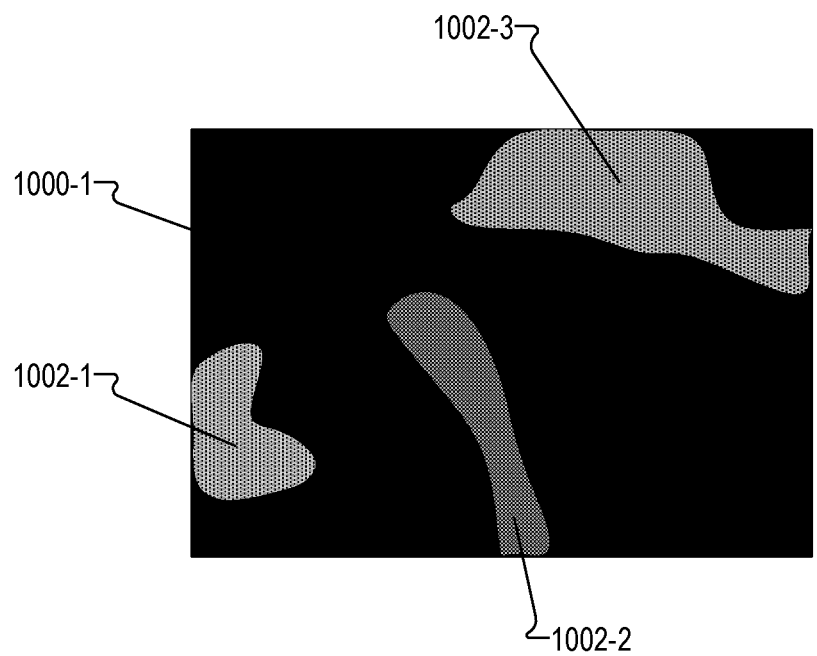
FIG. 10 illustrates exemplary images that the tag management system may use to identify an image location at which a graphical tag representative of a fluorescence event may be rendered.
Figure 10:
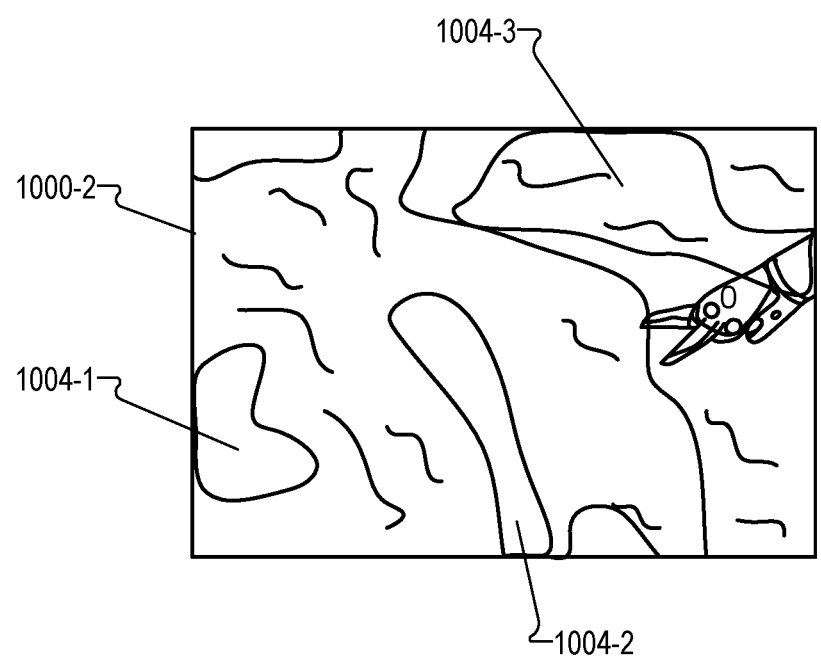
Figure 11:
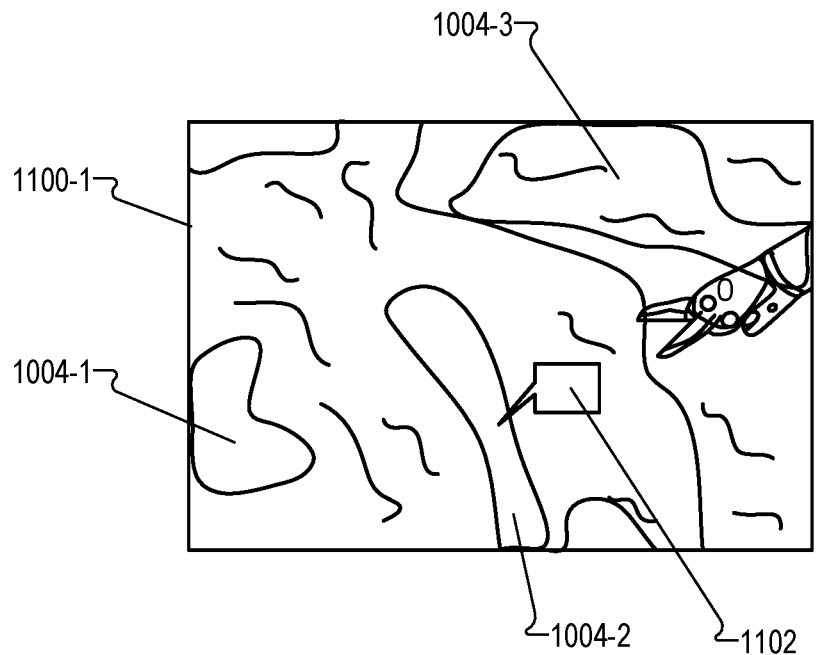
FIG. 11 illustrates exemplary images in which a graphical tag associated with a fluorescence event is rendered.
Figure 11:
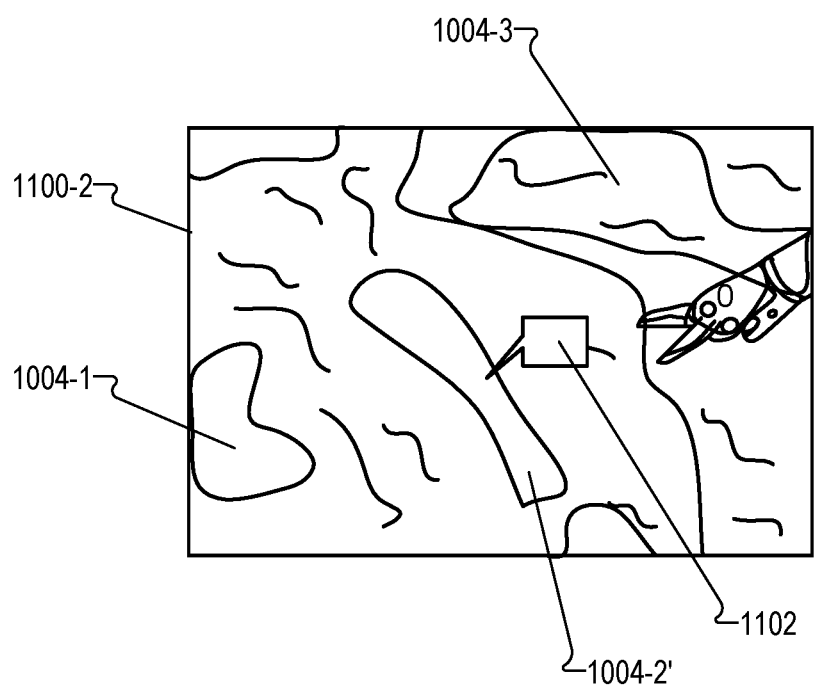

An exemplary manner of identifying, within a visible light image of the region of interest, an image location that depicts the fluorescence event location will now be described with reference to FIGS. 10 and 11. FIG. 10 illustrates exemplary images 1000-1 and 1000-2 that system 100 may use to identify an image location at which a graphical tag representative of a fluorescence event may be rendered. FIG. 11 illustrates exemplary images 1100-1 and 1100-2 in which a graphical tag associated with a fluorescence event is rendered.

Referring now to FIG. 10, image 1000-1 is a fluorescence image captured by an imaging device (e.g., imaging device 302) aimed at a region of interest (e.g., an internal space of a patient), and may be represented by fluorescence image data (e.g., fluorescence image data 404). Fluorescence image 1000-1 includes a plurality of fluorescing regions 1002 (e.g., fluorescing regions 1002-1 through 1002-3). Image 1000-2 is a visible light image captured by the imaging device (or another imaging device) simultaneously with the capture of fluorescence image 1000-1 and may be represented by visible light image data (e.g., image data 306). Image 1000-2 includes a plurality of image objects 1004 (e.g., image objects 1004-1 through 1004-3) that depict anatomical features within the region of interest.

System 100 may determine that a fluorescence event occurs by determining, in any way described herein, that a contrast level of fluorescence image 1000-1 is within an optimum range. System 100 may then identify, within visible light image 1000-2, an image location that depicts the fluorescence event location. For example, system 100 may segment fluorescence image 1000-1 to identifying fluorescing regions 1002. System 100 may also segment visible light image 1000-2 to identify image objects 1004. System 100 may identify a particular image object 1004 within visible light image 1000-2 that corresponds to (e.g., has the same image location as) a fluorescing region 1002 in fluorescence image 1000-1. System 100 may then designate the identified image object within visible light image 1000-2 as the image object representative of the fluorescence event. In the example of FIG. 10, system 100 may determine that only fluorescing region 1002-2 is within the optimum range and thus designate image object 1004-2 within image 100-2 as the designated image object. System 100 may store data representative of image object 1004-2 as tag data associated with the fluorescence event.

FIG. 11 shows exemplary visible light images 1100-1 and 1100-2 that may be captured by the imaging device and include a graphical tag 1102 representative of the fluorescence event. Image 1100-1 is the same as visible light image 1000-2 except that system 100 has rendered graphical tag 1102 within visible light image 1100-1 at an image location of image object 1004-2.

Image 1100-2 may be captured by the imaging device subsequently to the fluorescence event (and subsequently to capture of image 1100-1). As shown in image 1100-2, image object 1004-2' has moved within the region of interest so that it is not at the same position as when image 1100-1 was captured (even though the imaging device has not moved within the region of interest). Nevertheless, system 100 may segment image 1100-2 and determine that image object 1004-2' matches the stored tag data representative of the designated image object. Accordingly, system 100 may render graphical tag 1102 at a new image location of image object 1004-2'.

When system 100 determines that a fluorescence event occurs, system 100 may identify a fluorescence image captured when the fluorescence event occurs (e.g., a fluorescence image that depicts the region of interest when the fluorescence event occurs) and associate the fluorescence image with the tag. For example, system 100 may associate fluorescence image 1000-1 with the tag representative of the fluorescence event. In this way, as will be explained below, fluorescence image 1000-1 may be accessed by a user and viewed at any time.

As explained above, system 100 may render the graphical tag within an image at an image location that depicts a surface of a physical location within the region of interest. In some examples, the image may be presented within a graphical user interface ("GUI") associated with a computer-assisted surgical system. The GUI may be presented by any display device described herein. For example, user control system 204 of surgical system 200 may present, by way of a stereo viewer or other display system, a GUI that a user (e.g., surgeon 210-1) may use to interact with surgical system 200. The GUI may include a main presentation window in which images (e.g., a video stream) captured by an imaging device (e.g., imaging device 302) coupled to a manipulator arm 212 may be presented to the user. Additionally or alternatively, the GUI may be presented by display monitor 214, by a mobile device communicatively paired with surgical system 200, and/or by any other display device associated with surgical system 200.

In some examples, the GUI may include, in a region outside of the main presentation window, one or more additional or other graphical elements to facilitate user interaction with the surgical system and/or access content associated with the surgical system and/or surgical session. The additional graphical elements may be configured to present information to the user (e.g., system information, surgical session information, additional content, etc.) and/or receive user input.

Figure 12:
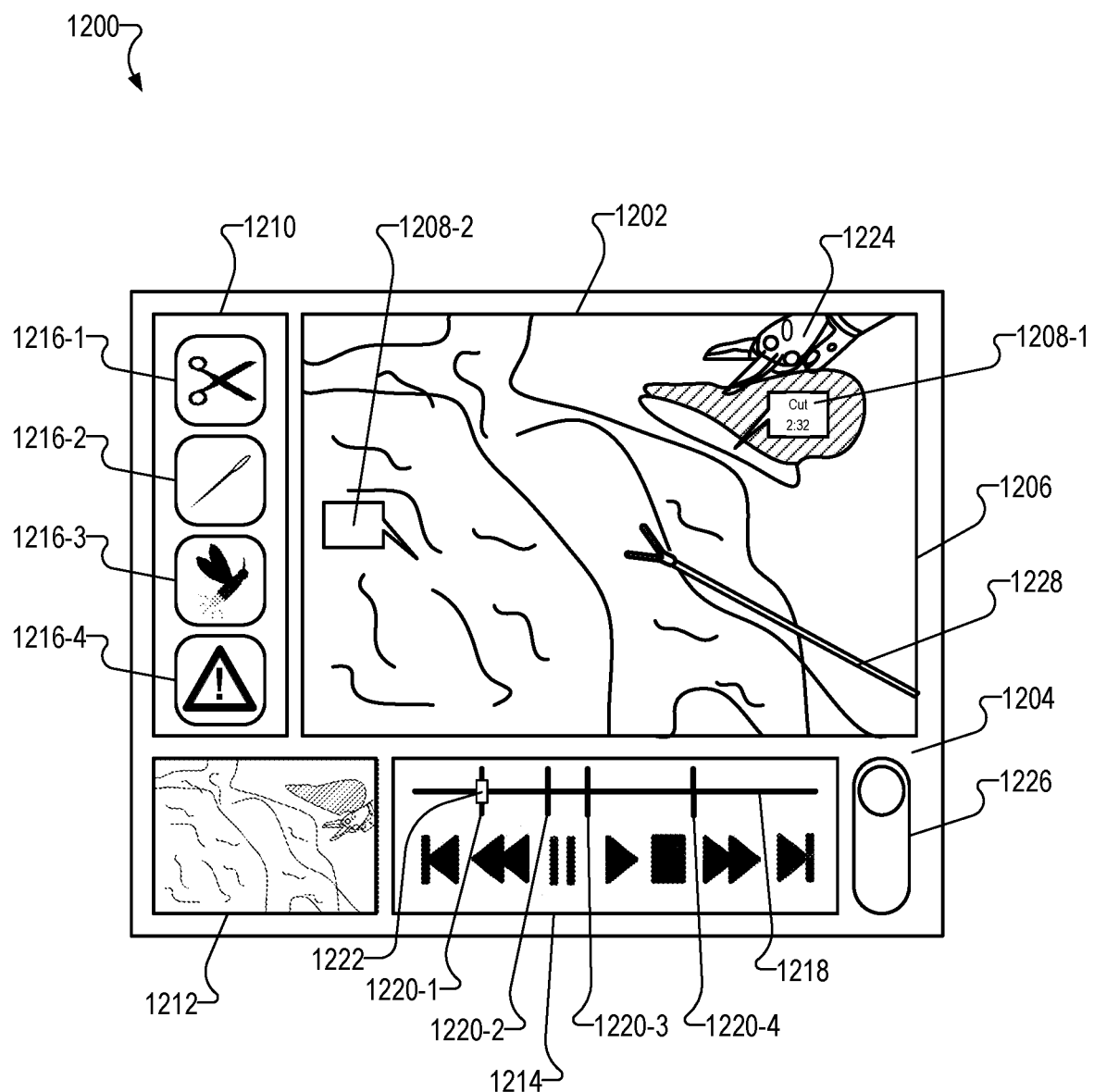
FIG. 12 illustrates an exemplary graphical user interface that may be associated with a computer-assisted surgical system.

In some examples, system 100 may render, within the region outside of the main presentation window, a graphical element representative of an event. FIG. 12 illustrates an exemplary GUI 1200 that may be associated with a computer-assisted surgical system (e.g., surgical system 200). As shown, GUI 1200 includes a main presentation window 1202 and a peripheral region 1204. Main presentation window 1202 presents one or more images (e.g., an image stream) captured by an imaging device. For example, an image 1206 is presented within main presentation window 1202. Image 1206 includes graphical tags 1208 (e.g., a graphical tag 1208-1 representative of a cutting event and a graphical tag 1208-2 representative of a needle drop event).

Peripheral region 1204 includes a tag icon region 1210, an auxiliary presentation window 1212, and a playback control panel 1214. GUI 1200 may include any additional or alternative elements as may suit a particular implementation.

Icon region 1210 includes a plurality of tag icons 1216 each associated with a particular graphical tag and/or detected event that occurs during a surgical session. The design (e.g., shape, form, color, etc.) of each tag icon 1216 may be representative of the type of event with which the tag icon 1216 is associated. For example, scissors icon 1216-1 may be representative of a cutting event, needle icon 1216-2 may be representative of a needle drop event, firefly icon 1216-3 may be representative of a fluorescence event, and warning icon 1216-4 may be representative of a tissue contact event (e.g., detection of contact of an imaging device with tissue). If an event is also represented by a graphical tag, the tag icon 1216 may also be associated with the corresponding graphical tag. For example, tag icon 1216-1 may be associated with graphical tag 1208-1 and tag icon 1216-2 may be associated with graphical tag 1208-2. Graphical tags associated with tag icons 1216-3 and 1216-4 may be out of the current view of the imaging device. System 100 may generate a tag icon 1216 in response to a determination that an event occurs within the region of interest. Data representative of the tag icon may be stored as tag data representative of the event.

Auxiliary presentation window 1212 is configured to present tag information and/or content associated with a tag, as will be described below in more detail. While auxiliary presentation window 1212 is shown to be located within peripheral region 1204, auxiliary presentation window 1212 may alternatively be a picture-in-picture window within main presentation window 1202.

Playback control panel 1214 is configured to enable a user to control playback of content presented within main presentation window 1202 and/or auxiliary presentation window 1212. Additionally or alternatively, playback control panel 1214 may be configured to enable a user to control playback of audio content. Playback control panel 1214 includes a set of playback control buttons (e.g., fast forward, skip, pause, play, rewind, stop, etc.) and a timeline 1218. Timeline 1218 includes a plurality of tag markers 1220 representative detected events and/or representative of graphical tags 1208 and/or tag icons 1216 associated with detected events. For example, tag marker 1220-1 is associated with graphical tag 1208-1 and tag icon 1216-1, tag marker 1220-2 is associated with graphical tag 1208-2 and tag icon 1216-2, tag marker 1220-3 is associated with tag icon 1216-3, and tag marker 1220-4 is associated with tag icon 1216-4. Tag markers 1220 are positioned along timeline 1218 based on the timestamp of the associated event (e.g., based on tag data). Timeline 1218 also includes a playback position marker 1222 that indicates a current playback location of content that is controlled by playback control panel 1214.

In some examples, timeline 1218 highlights or shows only tag markers 1220 that are associated with event locations or events having an event location that is within a current active region. An active region may refer to a portion of the region of interest where activity (e.g., operations of the computer-assisted surgical system) is currently taking place. An active region may be, for example, a region that is within a field of view of the imaging device (or that is depicted in the presently displayed image 1206), a region that is within a predetermined distance of an instrument (e.g., a surgical instrument that is currently being manipulated), a region that is within a gaze of the user (as determined by a gaze tracking system), a region depicted within a predetermined area of main presentation window 1202, or any other suitable region. As the active region changes (e.g., the imaging device moves, a manipulated instrument moves, the user's gaze moves, etc.), the tag markers that are shown on timeline 1218 may change (e.g., disappear, appear, or change form (e.g., shape, color, size, transparency, etc.)) depending on which event locations are within the updated active region or depicted in a subsequently captured image. Similarly, icon region 1210 highlights or shows only tag icons 1216 that are associated with event locations or events having an event location that is within the current active region. As the active region changes, the tag icons that are shown in icon region 1210 may change (e.g., disappear, appear, or change form (e.g., shape, color, size, etc.)) depending on which event locations are within the updated active region or depicted in a subsequently captured image.

In some examples, the form of tag icons 1216 and/or tag markers 1220, as well as of graphical tags 1208, may change gradually depending on the proximity of the associated event location to the current active region. For example, the opacity of a graphical tag element (e.g., a tag icon 1216, a tag marker 1220, and/or a graphical tag 1208) may increase as the active region gets nearer to the event location associated with the graphical tag element. Similarly, the transparency of the graphical tag element may increase as the active region moves away from the event location associated with the graphical tag element. In alternative embodiments, the opacity may increase as the distance between the active region and the event location increases, and the transparency may increase as the distance between the active region and the event location decreases.

As mentioned, system 100 may provide a user with access to content associated with a graphical tag and/or a particular physical location (e.g., an event location) within a region of interest. For example, a graphical tag 1208, tag icon 1216, and/or tag marker 1220 may be configured to provide a user with access to information and/or content associated with the tag and/or event location. For example, system 100 may detect a user interaction with a particular graphical tag 1208, tag icon 1216, or tag marker 1220 (each generally referred to as a "graphical tag element") and present, in response to detection of the user interaction, information and/or content associated with the particular graphical tag element.

The user interaction may include any suitable type of user interaction with a graphical tag element. In some examples, the user interaction comprises a selection of the graphical tag element with a selector that is rendered in the GUI and movable by the user. The selector may be a depictions of a real, physical object located within the region of interest, such as surgical instrument 1224 depicted within image 1206, a user's finger (e.g., when GUI 1200 is presented by a touchscreen display device or when GUI 1200 is presented by an AR or VR headset). Alternatively, the selector may be synthetic, such as a cursor displayed in GUI 1200, a virtual surgical instrument depicted within image 1206, a virtual object within an AR or VR display, and/or any other synthetic selector.

The user interaction may be any type of interaction with the graphical tag element. A manual selection of the graphical tag element may include, for example, a user positioning the selector on or near the graphical tag element and actuating a button on a user-input device (e.g., a button on user control system 204, a button on the set of master controls of user control system 204), hovering over the graphical tag element (e.g., hovering surgical instrument 1224 over graphical tag 1208-1 for a predetermined period of time), a predefined gesture with respect to a graphical tag element (e.g., a swipe or pinch gesture by a user on a touchscreen display device, a predetermine motion of surgical instrument 1224, etc.), and any other suitable type of interaction. In some examples, system 100 may also automatically select the graphical tag element when the selector is moved within a predetermined vicinity of the graphical tag element. For example, surgeon 210-1 may move surgical instrument 1224 within a predetermined vicinity of graphical tag 1208-1 while performing a surgical procedure. System 100 may determine that surgical instrument 1224 is within a predetermined distance of graphical tag 1208-1 and thus automatically select graphical tag 1208-1.

Upon selection of a graphical tag element, system 100 may present information and/or content associated with the graphical tag element. System 100 may present the information and/or content in any suitable way and in any suitable location. For example, the information and/or content (or a thumbnail image of the content) may be presented directly within the graphical the tag element, as illustrated in graphical tag 1208-1 (showing a brief event description and timestamp). In the example of FIG. 12, content associated with the selected graphical tag 1208-1 (e.g., image 700-1) is also presented within auxiliary presentation window 1212.

In some examples multiple different content instances may be associated with a particular tag. Although not shown in FIG. 12, GUI 1200 may provide an option for the user to select which particular content instance is to be presented upon selection of the graphical tag element.

In some examples, the content may additionally or alternatively be presented in main presentation window 1202. For example, a recorded video stream may be played back in main presentation window 1202 upon selection of an associated graphical tag element. In some examples, when associated content is presented in main presentation window 1202, the live video feed that was presented in main presentation window 1202 may be switched to auxiliary presentation window 1212, thereby allowing the user to have continuous access to view the live video feed without disruption and also mitigate risks associated with presenting associated content. In some examples, system 100 may also automatically switch the live video feed back to presentation within main presentation window 1202 when surgical instruments are moved (or when certain surgical instruments are moved, such as surgical instruments with tissue interaction functionality).

As mentioned, a fluorescence image (e.g., fluorescence image 1000-1) associated with a fluorescence event may be accessed by way of a graphical element (e.g., a graphical tag and/or tag icon 1216-3) and viewed at any time. In some examples, system 100 may present the fluorescence image within auxiliary presentation window 1212. In alternative examples, system 100 may present the fluorescence image within main presentation window 1202. This may occur when, for example, the imaging device has the same pose (e.g., 3D position and orientation) within the region of interest as when the fluorescence image was captured. The pose of the imaging device may be stored as tag data when the fluorescence event is detected. In some examples, system 100 may be configured to indicate (such as by highlighting or flashing tag icon 1216-3) when a pose of the imaging device is the same (or similar) as the pose of the imaging device when the fluorescence event occurred. Additionally or alternatively, system 100 may be configured to control the positioning of the imaging device based on the stored tag data (e.g., move the imaging device so that it has same pose indicated by the tag data). When a fluorescence image is presented, the fluorescence image may be presented independently of any other image, or it may be combined with a contemporaneous visible light image (e.g., as a composite image or augmented image).

In some examples, system 100 may provide a user with access to content associated with a physical location (e.g., an event location) based on proximity of an instrument to the physical location. For instance, system 100 may provide a user with access to the content when the physical location is within a field of view of the imaging device. System 100 may provide the user with access to the content by way of a graphical tag element associated with the event location when the event location is depicted in a currently presented image (e.g., is within a field of view of the imaging device).

As another example, system 100 may provide a user with access to the content when an instrument (real or virtual) is determined to be within a predetermined distance of the event location. The instrument may be an imaging device, or the instrument may be an instrument other than the imaging device. To illustrate, when a graspers instrument passes by a location where a needle was previously dropped, system 100 may provide access to video and/or image content showing the needle drop event.

System 100 may provide access to the content in any way described herein. In some examples, system 100 may provide access to content by automatically presenting the content or by providing a graphical tag element or other user selectable option configured to initiate presentation of the content in response to a user interaction with the graphical tag element or user selectable option. In some examples, system 100 provides, at a current time after a prior time when an event occurred, access to content associated with the event or event location without rendering, at the current time, a graphical tag associated with the event or event location. For example, system 100 may provide access to the content by way of tag icon 1216, tag marker 1220, and/or another selectable option within GUI 1200.

In some examples, an event may occur outside the field of view of the imaging device but nevertheless be detected by system 100 based on surgical session data (e.g., based on kinematic data, sensor data, changes in image data (e.g., a needle is shown in a first frame but is not shown in a subsequent frame), etc.). For example, system 100 may detect contact of an imaging device with tissue, dropping a grasped object (e.g., a surgical mesh), etc. System 100 may identify a 3D event position of such event and associate content (e.g., an event description, an alert, etc.) with the 3D event position. System 100 may then provide a user with access to the content when the 3D event position is within the field of view of the imaging device and/or when an instrument is within a predetermined distance of the 3D event position. In this way, a user may be alerted to unseen events that the user did not see and did not know had occurred.

In some examples, when associated content is presented in main presentation window 1202 or auxiliary presentation window 1212, system 100 may initiate one or more mitigation operations to mitigate risks associated with a user having access to view content other than a live video feed within main presentation window 1202. For example, system 100 may present one more visual effects (e.g., animating surgical instruments within a recorded video clip, false coloring image features, dimming the images, etc.), warnings, or notices with the associated content to clearly identify the associated content as not being the live video feed. Additionally or alternatively, system 100 may disable use of surgical instruments, or use of certain functions of surgical instruments (e.g., grasping, energization, stapling, etc.) while associated content is presented. As another example, system may provide haptic feedback (e.g., vibration, etc.) to instruments when the surgical instruments are operated during presentation of the associated content.

System 100 may also be configured to allow a user to control the display of graphical tag elements, e.g., turn ON and/or turn OFF the presentation of graphical tag elements. System 100 may enable turning ON/OFF of graphical tag elements in any suitable way. In some examples, system 100 is configured to receive user input configured to display (e.g., turn ON and/or turn OFF) graphical tag elements. For instance, as shown in FIG. 12, GUI 1200 includes a global switch 1226 by which a user can turn ON and/or turn OFF the display of all graphical tags 1208 within the image presented in main presentation window 1202. Additionally or alternatively, a user can selectively turn ON and/or turn OFF the display of individual graphical tags 1208, such as by selecting a tag icon 1216 or selecting a selectable option (not shown) included within each graphical tag 1208.

In additional or alternative examples, graphical tags 1208 may be automatically turned ON/OFF based on a location of a selector to an event location. For instance, graphical tag 1208-1 may remain in an OFF state (or an ON state in an alternative example) until surgical instrument 1224 moves to a location within a predetermined distance of the event location associated with graphical tag 1208-1, in which case system 100 may switch graphical tag 1208-1 to an ON state (or to the OFF state). When surgical instrument 1224 moves beyond the predetermined distance, system 100 may switch graphical tag 1208-1 to the OFF state (or to the ON state).

Alternatively to automatically turning the graphical tag to an ON state when a surgical instrument is within the predetermined distance of the event location, system 100 may notify the user (e.g., visually, audibly, and/or haptically) of the proximity to the event location. For example, when surgical instrument 1224 moves within the predetermined distance of graphical tag 1208-1, system 100 may vibrate the set of master controls of user control system 204. Additionally or alternatively, the system 100 may visually identify the associated tag icon 1216-1 and/or tag marker 1220-1, such as by highlighting, false coloring, flashing, enlarging, or otherwise graphically drawing attention to tag icon 1216-1 and/or tag marker 1220-1. The user may then select the tag icon 1216-1 and/or tag marker 1220-1 to turn on graphical tag 1208-1 and/or to initiate presentation of content associated with graphical tag 1208-1. In this way, system 100 may automatically recommend and provide the user with access to content that might be of interest to the user and the user can easily review what events happened at certain locations, even when the user is not initially aware of the events.

In some examples, a user (e.g., surgeon 210-1) may manually control browsing of associated content and selection of tags by use of the set of master controls of user control system 204. For instance, instead of operating playback control panel 1214, the user may fast forward and/or rewind through video content and/or audio content by moving the set of master controls in a predefined manner (e.g., left or right) or with a predefined gesture. In some examples, the fast forward and rewind speeds, or the video playback speed, may be adjusted and controlled based on the force applied by the user to the set of master controls. In some examples, a haptic notification may be provided to the user when playback position marker 1222 reaches a tag marker 1220. The haptic notification may be, for example, a vibration of the set of master controls. In some examples, playback position marker 1222 may stop or temporarily pause each time a tag marker 1220 is reached. This may facilitate the user quickly finding tagged video content.

As mentioned above, system 100 may use tag data (e.g., tag data 504) to control operations of a medical system. Exemplary manners in which system 100 may use tag data to control operations of a medical system will now be described with reference to FIGS. 12-14.

As shown in FIG. 12, system 100 may render, within GUI 1200, a graphical tag element (e.g., graphical tag 1208, tag icon 1216, or tag marker 1220). The graphical tag element may be associated with a physical location (e.g., a tagged physical location) within a region of interest. As used herein, a physical location may be any real location, within a physical region of interest, that is associated with a tag and/or an event (e.g., an event location). A real location may be associated with a tag and/or an event in any of the ways described herein. A physical location may include, for example, a 3D position within the region of interest (e.g., a 3D event position), a physical location on a surface of a dynamic object located within the region of interest, and/or any other suitable physical location within the region of interest. Tag data representative of the tag may include data representative of the physical location, such as data representative of a 3D position (e.g., 3D event position) and/or data representative of a designated object (e.g., a cut region).

System 100 may detect an interaction, by a user, with the graphical tag element. The interaction may be any suitable user interaction described herein. For example, system 100 may detect a selection of graphical tag 1208-2.

Figure 13:
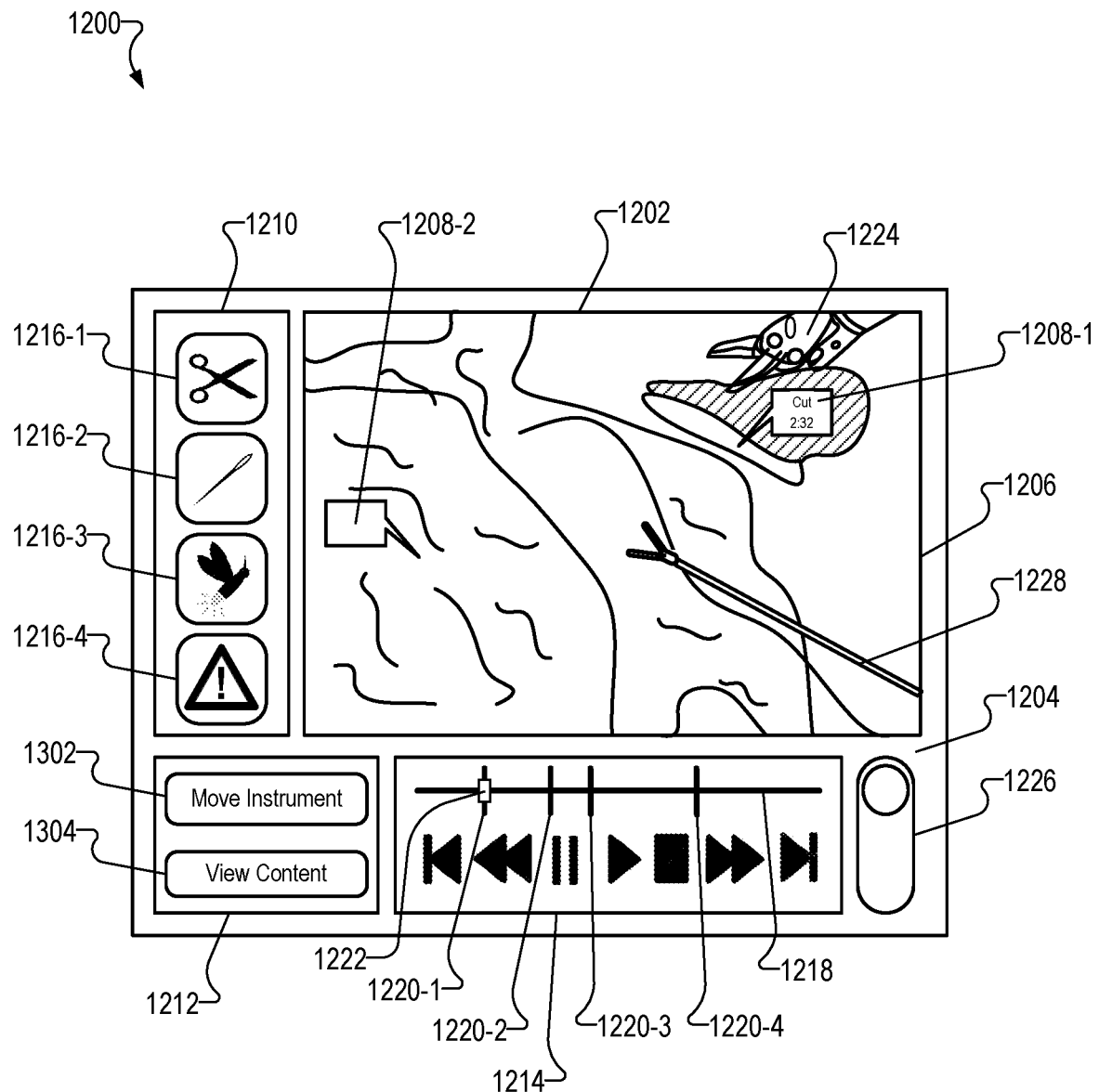
FIGS. 13-15 illustrate various additional views of the graphical user interface of FIG. 12.

In some examples, the interaction with the graphical tag element comprises an interaction with a selectable option associated with the graphical tag element and configured to initiate automatic control of the surgical instrument. FIG. 13 illustrates another view of GUI 1200 in which a first selectable option 1302 is presented within auxiliary presentation window 1212 in response to a first interaction with graphical tag 1208-2. It will be recognized that selectable option 1302 may additionally or alternatively be presented at any other location within GUI 1200, such as within graphical tag 1208-2 or within tag icon 1216-2. System 100 may then detect a second interaction by the user with selectable option 1302 to initiate automatic control (e.g., pose adjustment) of the surgical instrument. In this way, a user may view information and/or content associated with the selected graphical tag element before deciding whether to initiate automatic instrument control.

In response to detecting the user interaction with graphical tag element (e.g., graphical tag 1208-2 and/or selectable option 1302), system 100 may direct the computer-assisted medical system to adjust a pose of an instrument based on the physical location that is associated with the graphical tag element. In some examples, the instrument may be any instrument located within the region of interest. For instance, the instrument may be an instrument associated with the tag, such as an instrument that performed or was otherwise involved in the event associated with the tag. Alternatively, the instrument may be an imaging device that captured an image of the region of interest when the event occurred or an imaging device that is currently located within the region of interest. In additional examples, the instrument may be any instrument selected by a user (e.g., by way of GUI 1200, by way of user control system 204, etc.).

In other examples, the instrument may be an instrument that is not located in the region of interest. For instance, the instrument (e.g., an ultrasound probe) may be located external to a patient (e.g., external to a surgical area internal to a patient) during the surgical session. As another example, the instrument may be an instrument used in another surgical session performed after the surgical session in which the graphical tag element is generated and/or images of the region of interest are captured. For instance, the instrument may be an instrument used during a subsequent surgical session (e.g., a surgical session de-briefing, surgical procedure reconstruction, training another surgeon on a particular technique performed during the first surgical procedure, etc.). During the subsequent surgical session, the instrument is not located within the region of interest of the first surgical session (e.g., because all surgical instruments have been removed from the surgical area internal to the patient and the patient has been moved to a recovery room). The instrument may be a real or virtual instrument.

In the example of FIGS. 12 and 13, it will be assumed that the user has selected, by way of a user control system, grasping instrument 1228 within the region of interest.

As mentioned above, the pose of an instrument may refer to the position of the instrument within the reference 3D coordinate system, the orientation of the instrument, or both. The pose of the instrument may be adjusted in any suitable way.

Figure 14:
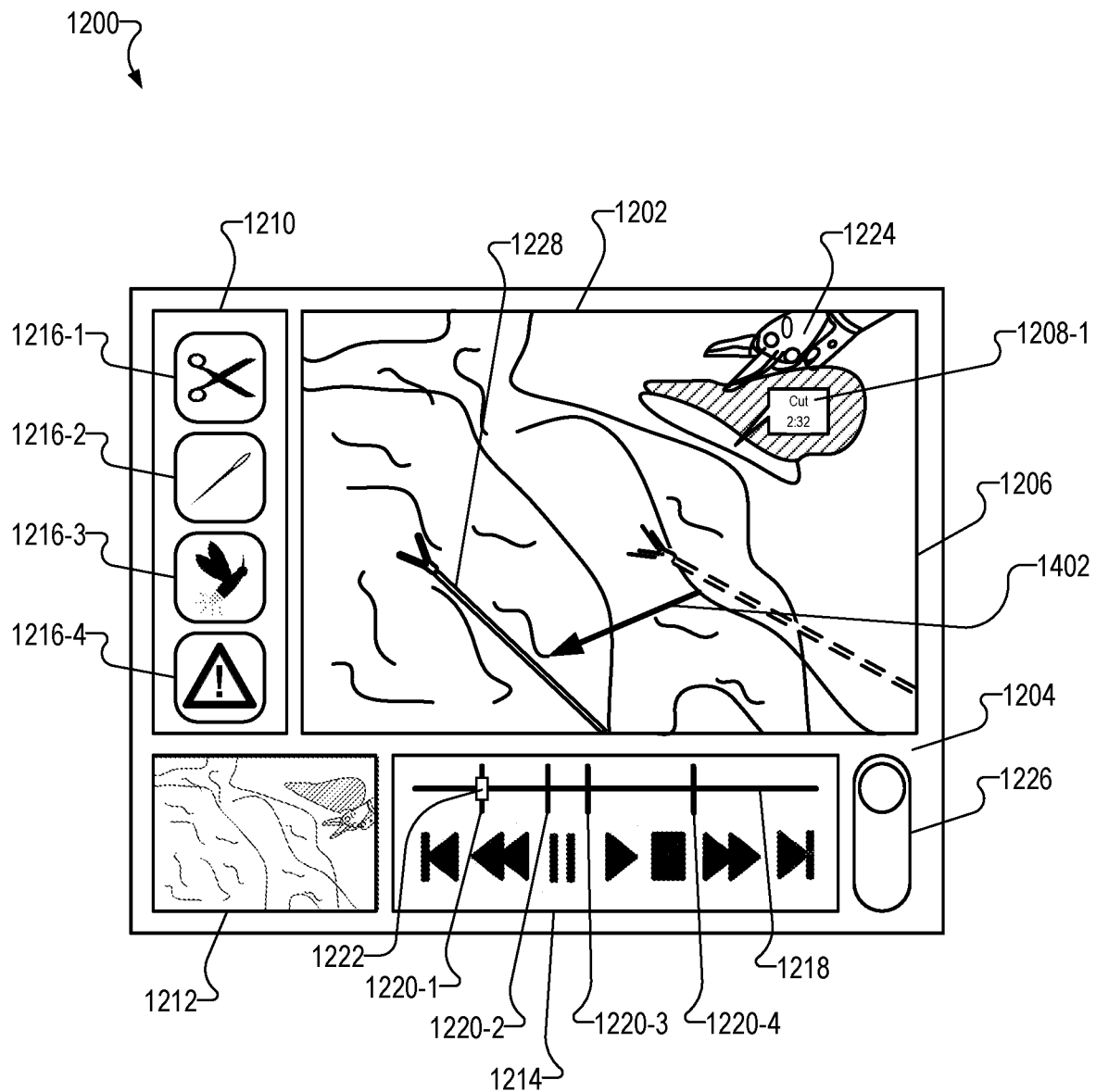

In some examples, the pose of the instrument may be adjusted by moving the instrument to the physical location within the region of interest or to a location within a vicinity (e.g., a predefined distance) of the physical location. For instance, the physical location may be a 3D position, within the region of interest, of an instrument when the event associated with the graphical tag element occurred at a prior time (e.g., a 3D event position of a needle driver when system 100 determined that the needle driver dropped a needle). The pose of the instrument may be adjusted by moving the instrument to the 3D position of the physical location within the region of interest. FIG. 14 illustrates another view of GUI 1200 in which the computer-assisted surgical has moved grasping instrument 1228 to the 3D position of the physical location associated with graphical tag 1208-2, as illustrated by arrow 1402. In response, system 100 has hidden (e.g., turned OFF) display of graphical tag 1208-2 so as to not obstruct the view of the region of interest. However, in some examples graphical tag 1208-2 may remain displayed unless turned OFF manually by the user.

When the physical location is a physical location on a surface of a dynamic object, the pose of the instrument may be adjusted based on the physical location by moving the instrument to the physical location on the surface of the dynamic object. If the physical location is depicted within a current image captured by an imaging device (e.g., is within a current field of view of the imaging device), system 100 may segment the image and use the tag data (e.g., data representative of the designated image object) to identify an image location, within the image, that depicts the physical location on the surface of a dynamic object. System 100 may then translate the image location to a 3D position, within the region of interest, of the physical location on the surface of the dynamic object. System 100 may perform this translation in any suitable way, such as by using a registration between the imaging device and the reference 3D coordinate system, a depth map of the region of interest, and/or a 3D model of anatomy located at the region of interest. System 100 may then move the instrument to the determined 3D position of the physical location on the surface of the dynamic object. In this way, the instrument may be moved to a physical location on a surface of a dynamic object even if the dynamic object has moved within the region of interest.

In some examples, however, the physical location may not be within the current field of view of the imaging device. To enable automatic adjustment of the pose of the instrument in such situations, system 100 may record, as tag data, the 3D event position of an instrument associated with the event (e.g., the imaging device) when the event occurs. System 100 may use the 3D event position to adjust a field of view of the imaging device to bring the physical location within the current field of view of the imaging device. Once the physical location is within the current field of view, of the imaging device, system 100 may then segment an image of the region of interest and identify the 3D position of the physical location within the region of interest, as described above. In this way, the instrument may be moved to a physical location on a surface of a dynamic object even if the dynamic object is not within the current view of the imaging device.

Figure 15:
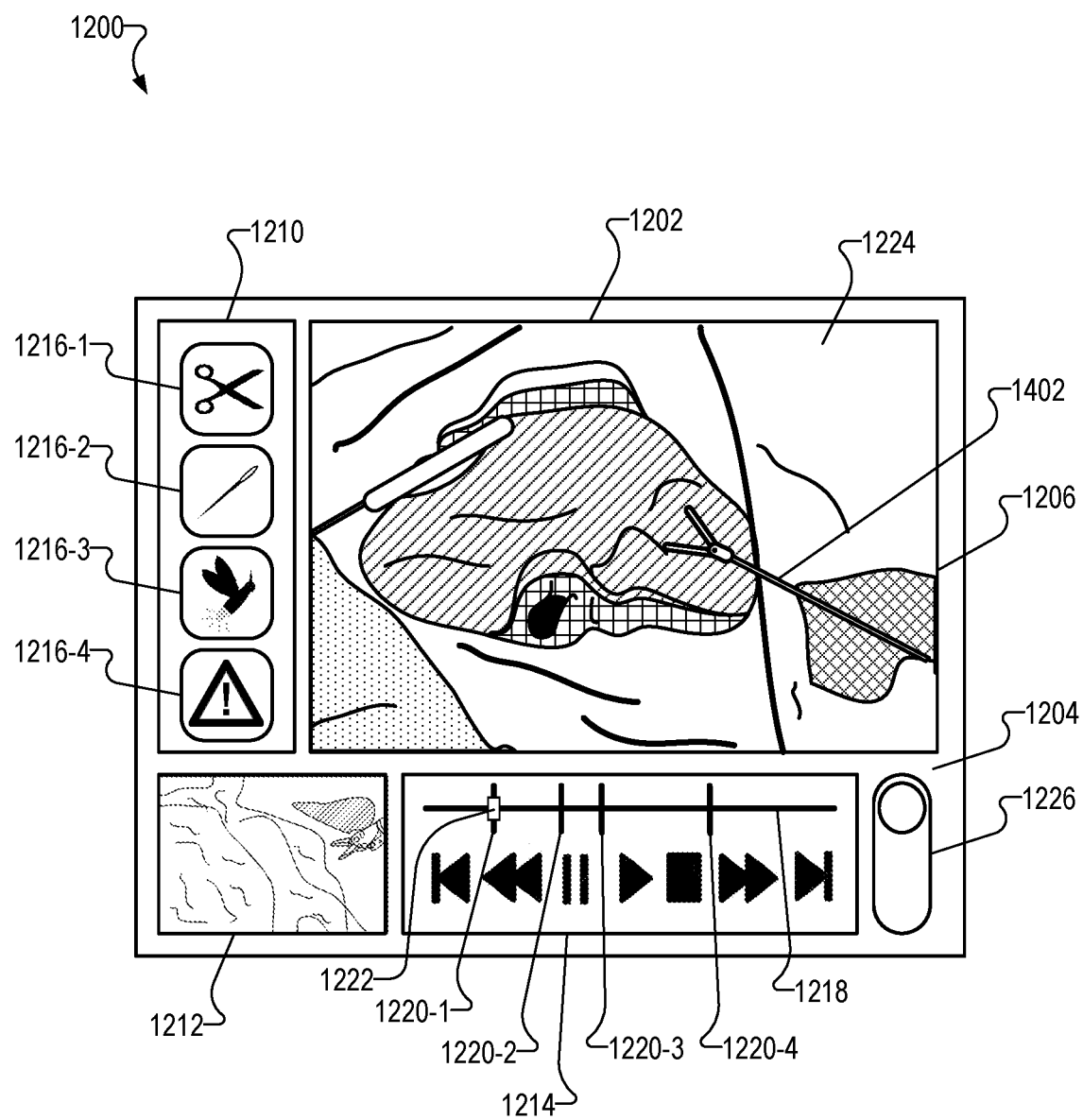

For example, FIG. 15 illustrates GUI 1200 at a current time and FIG. 12 illustrates GUI 1200 at a prior time (e.g., a time when a needle-drop event occurred within the region of interest). As shown in FIG. 15, the current field of view of the imaging device is different from the prior field of view of the imaging device at the prior time depicted in FIG. 12 and thus does not depict the physical location associated with graphical tag 1208-2. However, in response to an interaction with tag icon 1216-2, system 100 may adjust the current field of view of the imaging device to match the prior field of view of the imaging device at the prior time depicted in FIG. 12. System 100 may then determine, based on the currently-captured image, the 3D position of the physical location on the surface of the dynamic object, and move grasping instrument 1228 to the determined 3D position of the physical location on the surface of the dynamic object, as illustrated in FIG. 14.

As mentioned, the pose of the instrument may be additionally or alternatively adjusted by adjusting an orientation of the instrument. For example, when the instrument is an imaging device, system 100 may record, as tag data, the pose (e.g., position and/or orientation) and any other suitable imaging device settings (e.g., zoom) when the event associated with the tag occurred. At a later time, the pose of the imaging device and/or other imaging device settings may be adjusted such that a current field of view of the imaging device matches or corresponds to the field of view of the imaging device when the event occurred at a prior time. This may be useful, for example, when the user wants to view a previously-captured fluorescence image combined with a currently-captured image of the region of interest. By matching the current field of view of the imaging device with the prior field of view of the imaging device when a fluorescence event occurred at a prior time, the previously-captured fluorescence image may be accurately aligned with the currently-captured image.

In some examples, system 100 may detect another interaction, by the user, with the graphical tag element and, in response, present content associated with the graphical tag element within the graphical user interface. The content may be any suitable content, such as one or more images of the region of interest captured when the event occurred at the prior time. In some examples, the other interaction and the presentation of the content may occur prior to the adjustment of the pose of the instrument. For example, as shown in FIG. 13, system 100 may present another selectable option 1304 within auxiliary presentation window 1212 in response to a first interaction with a graphical tag element (e.g., graphical tag 1208-2). System 100 may detect another user interaction with selectable option 1304 and, in response, present (e.g., within main presentation window 1202 and/or auxiliary presentation window 1212) content associated with the selected graphical tag element. In this way, the user may view the content associated with the graphical tag element before deciding whether the pose of the instrument should be adjusted. In other examples, the other interaction and the presentation of the content may occur after the adjustment of the pose of the instrument. For example, as explained above a fluorescence image associated with the graphical tag element may be combined with a current image of the region of interest after the field of view of the imaging device has been adjusted to match the field of view when a fluorescence event occurred.

In the examples described above, system 100 may direct a computer-assisted surgical system to adjust a pose of an instrument based on the physical location within the region of interest. In additional examples, system 100 may also direct the computer-assisted surgical system to move and/or adjust, based on the physical location, a pose of a user input device that is configured to control the instrument. For instance, system 100 may direct the computer-assisted surgical system to move and/or adjust a set of master controls in a manner that would have effected the same automatic adjustment of the pose of the instrument by system 100.

Figure 16:
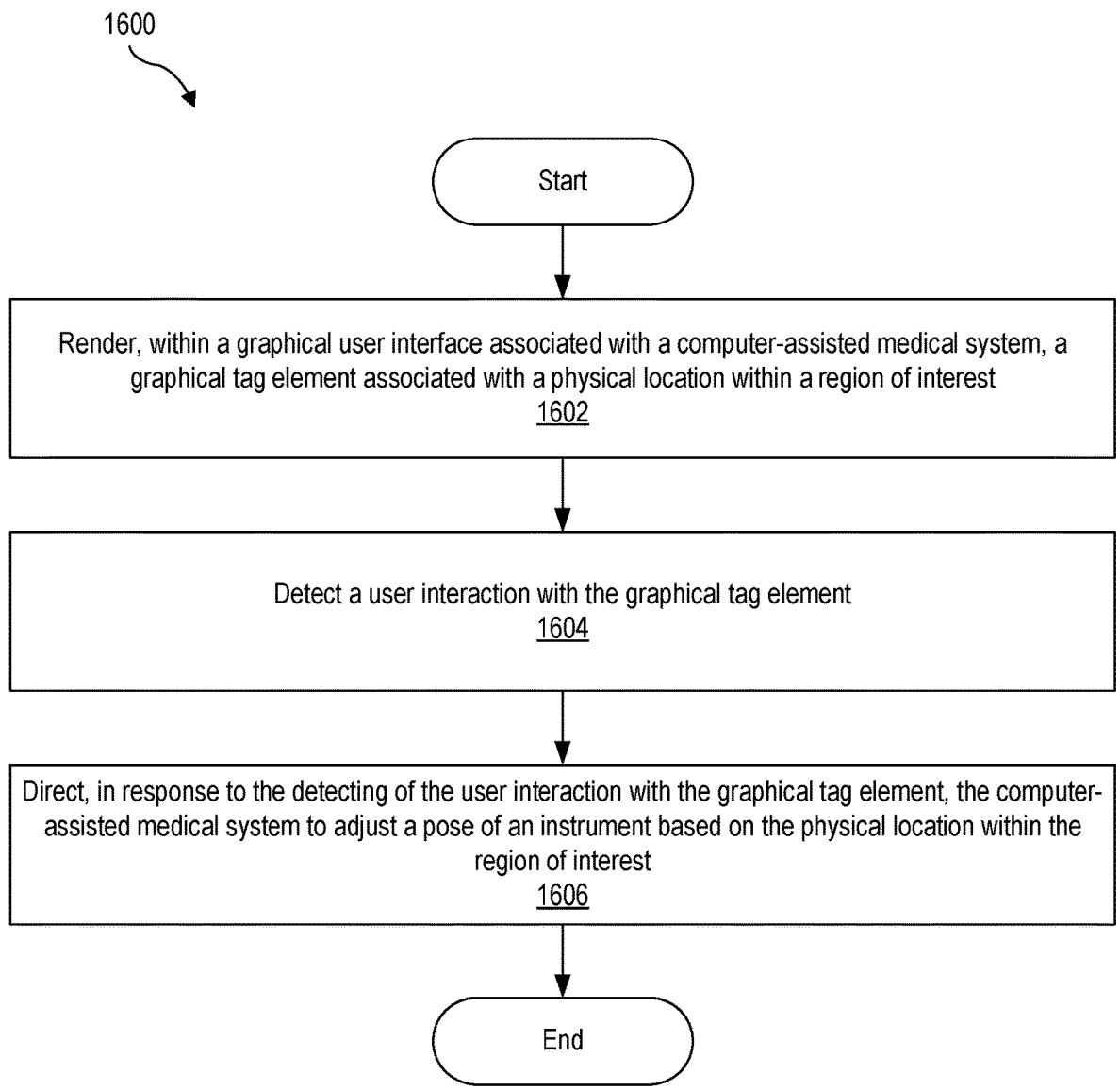
FIG. 16 illustrates an exemplary method of tag-based instrument control.

FIG. 16 illustrates an exemplary method 1600 of tag-based instrument control. While FIG. 16 illustrates exemplary operations according to one embodiment, other embodiments may omit, add to, reorder, and/or modify any of the operations shown in FIG. 16. One or more of the operations shown in FIG. 16 may be performed by system 100, any components included therein, and/or any implementation thereof.

In operation 1602, a graphical tag element may be rendered within a graphical user interface associated with a computer-assisted medical system. The graphical tag element may be associated with a physical location within a region of interest. Operation 1602 may be performed in any of the ways described herein.

In operation 1604, a user interaction with the graphical tag element may be detected. Operation 1604 may be performed in any of the ways described herein.

In operation 1606, in response to the detecting of the user interaction with the graphical tag element, the computer-assisted medical system may be directed to adjust a pose of an instrument located at the region of interest based on the physical location within the region of interest. Operation 1606 may be performed in any of the ways described herein.

Figure 17:
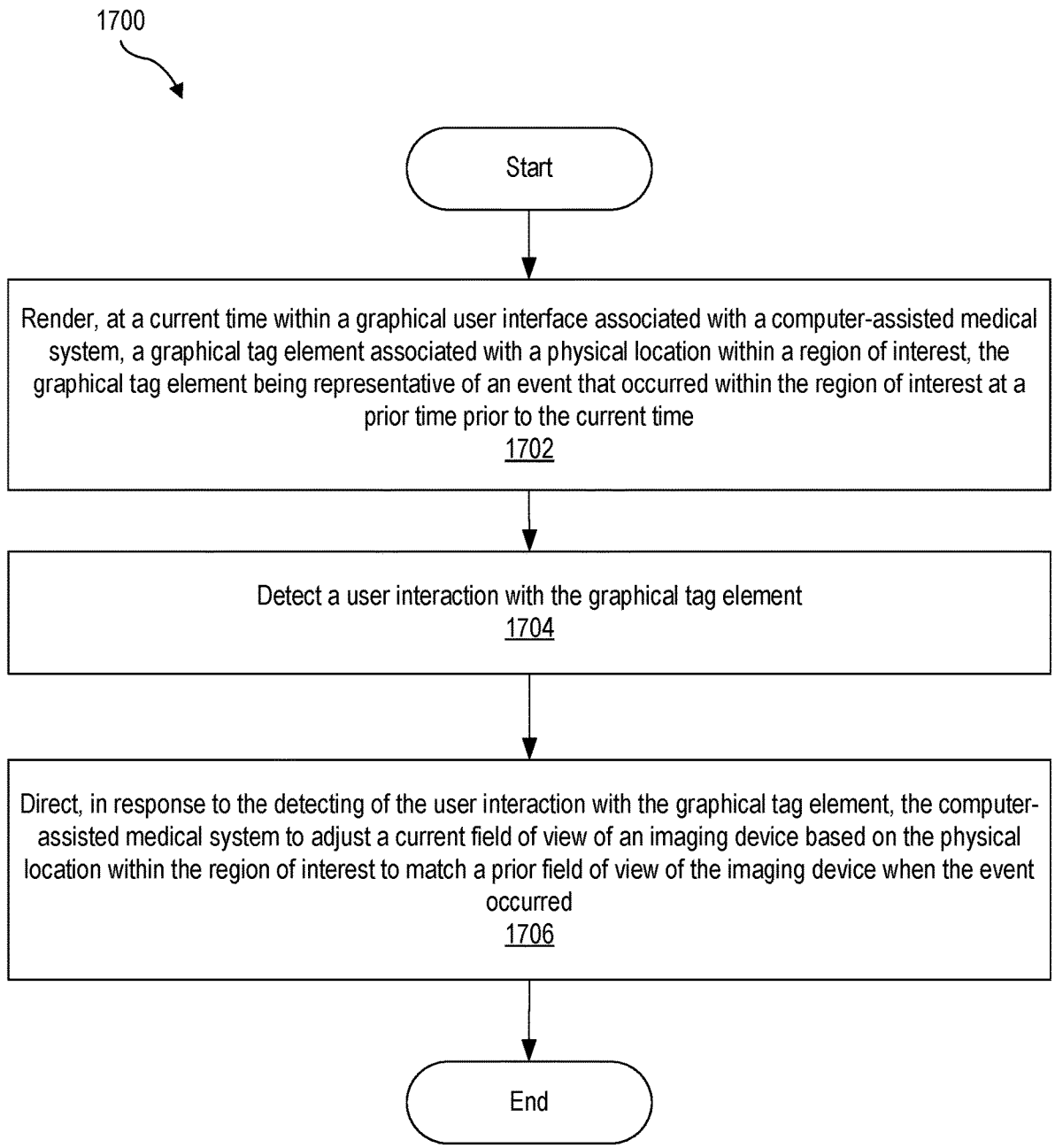
FIG. 17 illustrates another exemplary method of tag-based instrument control.

FIG. 17 illustrates another exemplary method 1700 of tag-based instrument control. While FIG. 17 illustrates exemplary operations according to one embodiment, other embodiments may omit, add to, reorder, and/or modify any of the operations shown in FIG. 17. One or more of the operations shown in FIG. 17 may be performed by system 100, any components included therein, and/or any implementation thereof.

In operation 1702, a graphical tag element may be rendered, at a current time, within a graphical user interface associated with a computer-assisted medical system. The graphical tag element may be associated with a physical location within a region of interest and may be representative of an event that occurred within the region of interest at a prior time prior to the current time. Operation 1702 may be performed in any of the ways described herein.

In operation 1704, a user interaction with the graphical tag element may be detected. Operation 1704 may be performed in any of the ways described herein.

In operation 1706, in response to the detecting of the user interaction with the graphical tag element, the computer-assisted medical system may be directed to adjust a current field of view of an imaging device based on the physical location within the region of interest to match a prior field of view of the imaging device when the event occurred. Operation 1706 may be performed in any of the ways described herein.

Figure 18:
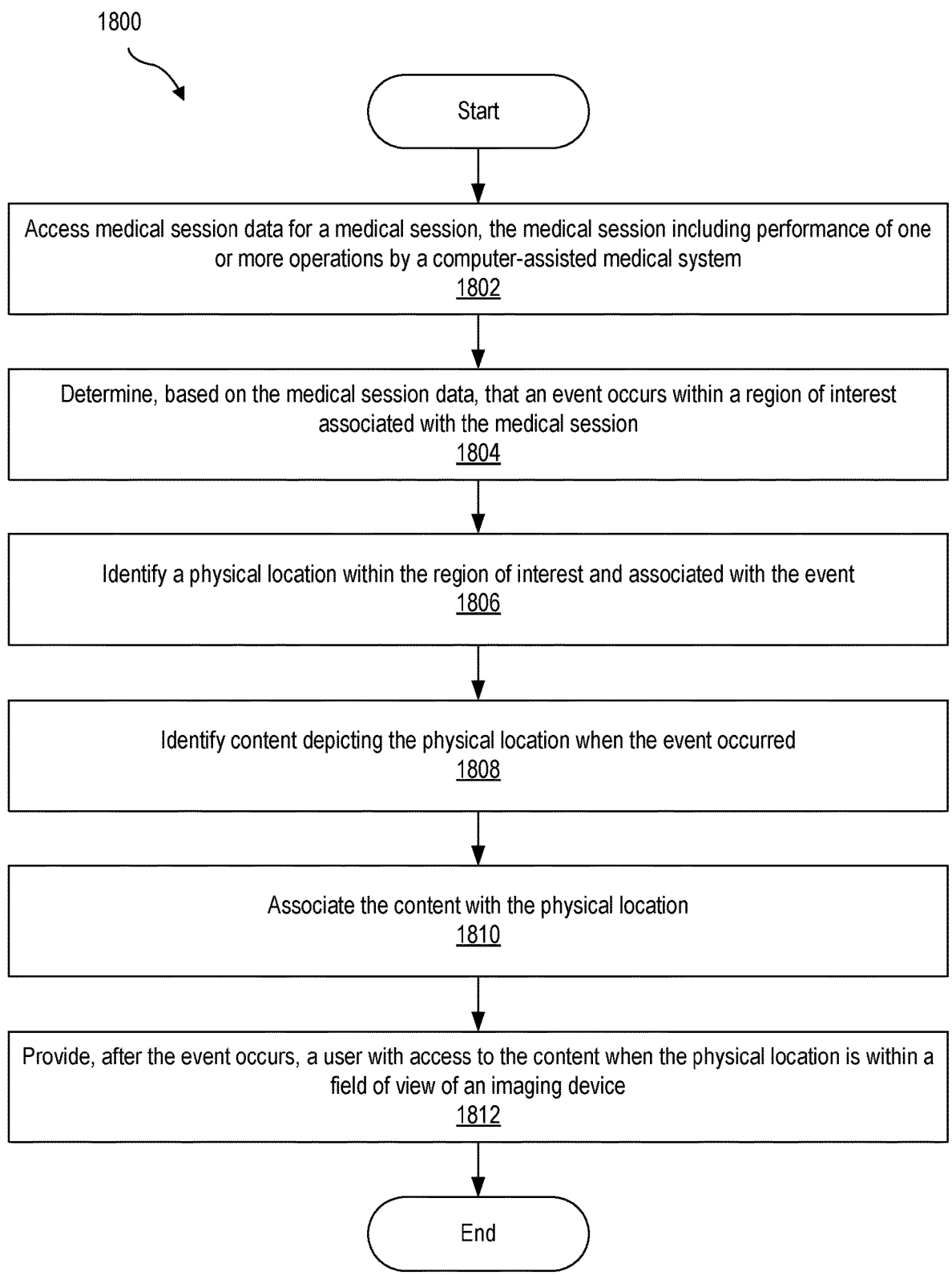
FIG. 18 illustrates an exemplary method of providing a user with access to content associated with a physical location within a region of interest.

FIG. 18 illustrates an exemplary method 1800. While FIG. 18 illustrates exemplary operations according to one embodiment, other embodiments may omit, add to, reorder, and/or modify any of the operations shown in FIG. 18. One or more of the operations shown in FIG. 18 may be performed by system 100, any components included therein, and/or any implementation thereof.

In operation 1802, system 100 may access medical session data (e.g., surgical session data) for a medical session (e.g., a surgical session). The medical session may include performance of one or more operations by a computer-assisted medical system (e.g., a computer-assisted surgical system, such as surgical system 200). Operation 1802 may be performed in any of the ways described herein.

In operation 1804, system 100 may determine, based on the medical session data, that an event occurs within a region of interest associated with the medical session. Operation 1804 may be performed in any of the ways described herein.

In operation 1806, system 100 may identify a physical location within the region of interest and associated with the event. Operation 1806 may be performed in any of the ways described herein.

In operation 1808, system 100 may identify content depicting the physical location when the event occurred. Operation 1808 may be performed in any of the ways described herein.

In operation 1810, system 100 may associate the content with the physical location. Operation 1810 may be performed in any of the ways described herein.

In operation 1812, system 100 may provide, after the event occurs, a user with access to the content when the physical location is within a field of view of an imaging device. Operation 1812 may be performed in any of the ways described herein.

Figure 19:
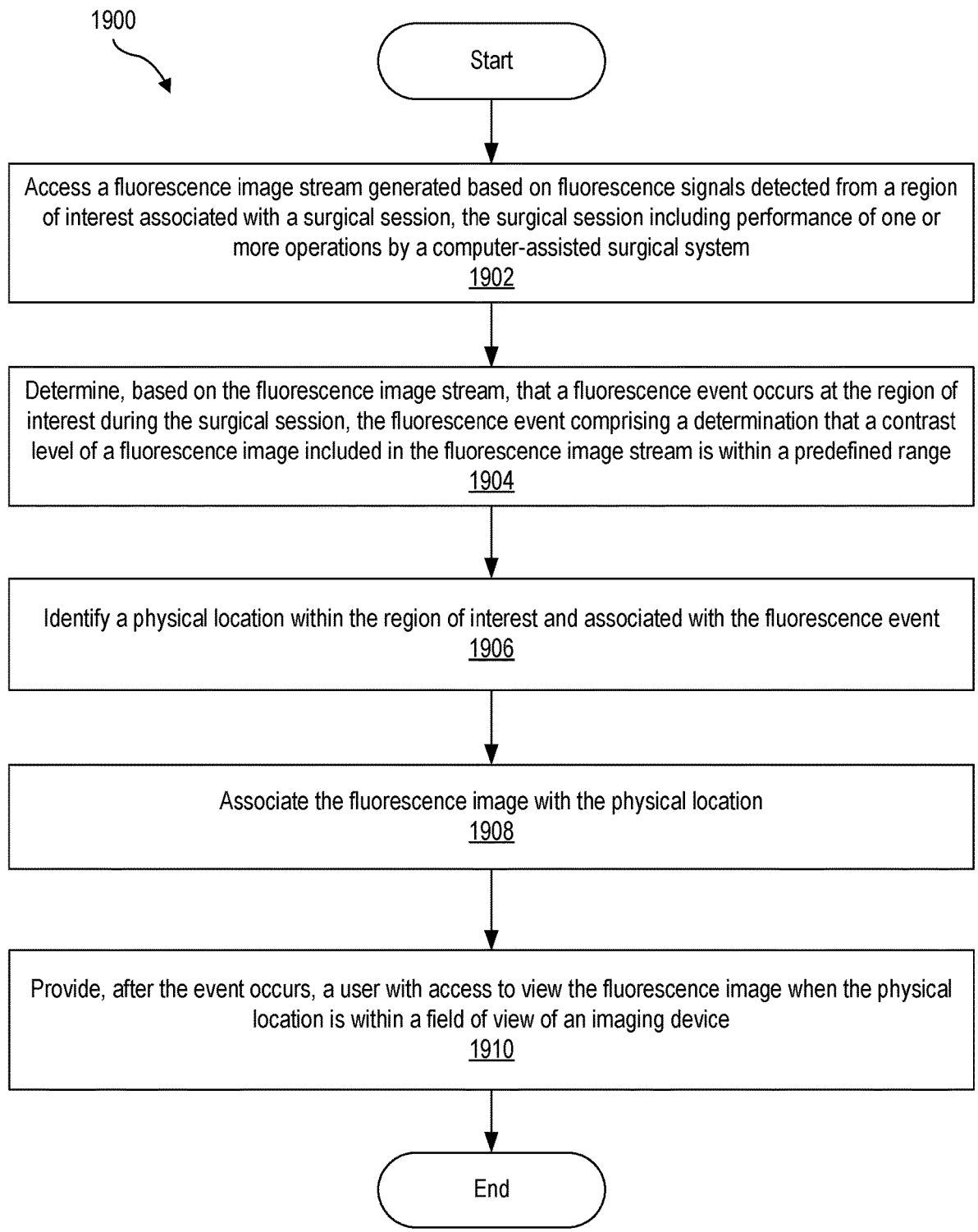
FIG. 19 illustrates an exemplary method of providing a user with access to a fluorescence image associated with a physical location within a region of interest.

FIG. 19 illustrates an exemplary method 1900. While FIG. 19 illustrates exemplary operations according to one embodiment, other embodiments may omit, add to, reorder, and/or modify any of the operations shown in FIG. 19. One or more of the operations shown in FIG. 19 may be performed by system 19, any components included therein, and/or any implementation thereof.

In operation 1902, system 100 may access a fluorescence image stream generated based on fluorescence signals detected from a surgical region of interest associated with a surgical session. The surgical session may include performance of one or more operations by a computer-assisted surgical system. Operation 1902 may be performed in any of the ways described herein.

In operation 1904, system 100 may determine, based on the fluorescence image stream, that a fluorescence event occurs at the surgical region of interest during the surgical session. The fluorescence event may comprise a determination that a contrast level of a fluorescence image included in the fluorescence image stream is within a predefined range. Operation 1904 may be performed in any of the ways described herein.

In operation 1906, system 100 may identify a physical location within the region of interest and associated with the fluorescence event. Operation 1906 may be performed in any of the ways described herein.

In operation 1908, system 100 may associate the fluorescence image with the physical location. Operation 1908 may be performed in any of the ways described herein.

In operation 1910, system 100 may provide, after the event occurs, a user with access to view the fluorescence image when the physical location is within a field of view of an imaging device. Operation 1910 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 20:
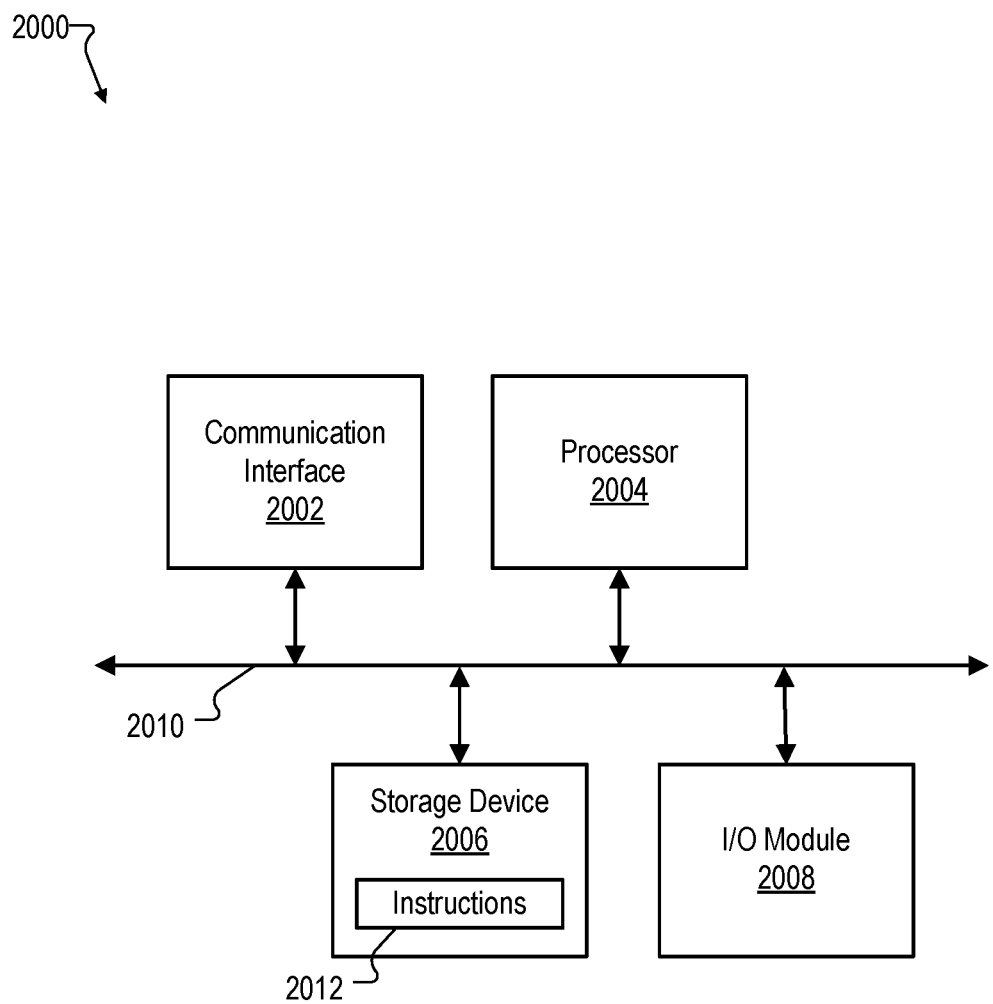
FIG. 20 illustrates an exemplary computing device according to principles described herein.

FIG. 20 illustrates an exemplary computing device 2000 that may be specifically configured to perform one or more of the processes described herein. As shown in FIG. 20, computing device 2000 may include a communication interface 2002, a processor 2004, a storage device 2006, and an input/output ("I/O") module 2008 communicatively connected one to another via a communication infrastructure 2010. While an exemplary computing device 2000 is shown in FIG. 20, the components illustrated in FIG. 20 are not intended to be limiting. Additional or alternative components may be used in other embodiments. Components of computing device 2000 shown in FIG. 20 will now be described in additional detail.

Communication interface 2002 may be configured to communicate with one or more computing devices. Examples of communication interface 2002 include, without limitation, a wired network interface (such as a network interface card), a wireless network interface (such as a wireless network interface card), a modem, an audio/video connection, and any other suitable interface.

Processor 2004 generally represents any type or form of processing unit capable of processing data and/or interpreting, executing, and/or directing execution of one or more of the instructions, processes, and/or operations described herein. Processor 2004 may perform operations by executing computer-executable instructions 2012 (e.g., an application, software, code, and/or other executable data instance) stored in storage device 2006.

Storage device 2006 may include one or more data storage media, devices, or configurations and may employ any type, form, and combination of data storage media and/or device. For example, storage device 2006 may include, but is not limited to, any combination of the non-volatile media and/or volatile media described herein. Electronic data, including data described herein, may be temporarily and/or permanently stored in storage device 2006. For example, data representative of computer-executable instructions 2012 configured to direct processor 2004 to perform any of the operations described herein may be stored within storage device 2006. In some examples, data may be arranged in one or more databases residing within storage device 2006.

I/O module 2008 may include one or more I/O modules configured to receive user input and provide user output. One or more I/O modules may be used to receive input for a single virtual experience. I/O module 2008 may include any hardware, firmware, software, or combination thereof supportive of input and output capabilities. For example, I/O module 2008 may include hardware and/or software for capturing user input, including, but not limited to, a keyboard or keypad, a touchscreen component (e.g., touchscreen display), a receiver (e.g., an RF or IR receiver), motion sensors, and/or one or more input buttons.

I/O module 2008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2008 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 2000. For example, processing facility 104 may be implemented by processor 2004 and storage facility 102 may be implemented by storage device 2006.

What is claimed is:

1. A system comprising:
a memory storing instructions; and
a processor communicatively coupled to the memory and configured to execute the instructions to:
determine, based on medical session data generated by a computer-assisted medical system, that an event occurred at a physical location within a region of interest;
identify, based on the medical session data, the physical location within the region of interest;
render, within a graphical user interface associated with the computer-assisted medical system, a graphical tag element representative of the event and the physical location within the region of interest;
detect a user interaction with the graphical tag element; and
direct, in response to the detecting of the user interaction with the graphical tag element, the computer-assisted medical system to adjust a pose of an instrument located at the region of interest based on the physical location within the region of interest.

2. The system of claim 1, wherein:
the physical location comprises a 3D position, within the region of interest, of the instrument when the event occurred; and
the adjusting of the pose of the instrument based on the physical location comprises moving the instrument to the 3D position of the physical location within the region of interest.

3. The system of claim 1, wherein:
the instrument comprises an imaging device; and
the adjusting of the pose of the instrument based on the physical location comprises adjusting a current field of view of the imaging device to match a prior field of view of the imaging device when the event occurred.

4. The system of claim 1, wherein the processor is further configured to execute the instructions to:
detect another interaction, by the user, with the graphical tag element; and
present, within the graphical user interface in response to the detection of the another interaction, content associated with the graphical tag element.

5. The system of claim 4, wherein:
the content comprises one or more images of the region of interest captured when the event occurred.

6. The system of claim 5, wherein:
the processor is further configured to access a fluorescence image stream generated based on fluorescence signals detected by an imaging device from the region of interest;
the event comprises a determination that a contrast level of a fluorescence image included in the fluorescence image stream is within a predefined range; and
the one or more images includes the fluorescence image.

7. The system of claim 1, wherein the rendering of the graphical tag element within the graphical user interface comprises rendering, within an image of the region of interest presented in the graphical user interface, a graphical tag at an image location that depicts the physical location.

8. The system of claim 1, wherein the rendering of the graphical tag element within the graphical user interface comprises rendering the graphical tag element in a region of the graphical user interface outside of a presentation of a visible light image stream depicting the region of interest.

9. The system of claim 1, wherein the user interaction with the graphical tag element comprises a user selection of the graphical tag element by way of a selector displayed in the graphical user interface.

10. A method for a tagging system comprising a memory storing instructions and a processor communicatively coupled to the memory and configured to execute the instructions to perform the method, the method comprising:
determining, by the tagging system based on medical session data generated by a computer-assisted medical system, that an event occurred at a physical location within a region of interest;
identifying, by the tagging system based on the medical session data, the physical location within the region of interest;
rendering, by the tagging system within a graphical user interface associated with the computer-assisted medical system, a graphical tag element representative of the event and the physical location within the region of interest;
detecting, by the tagging system, a user interaction with the graphical tag element; and
directing, by the tagging system in response to the detecting of the user interaction with the graphical tag element, the computer-assisted medical system to adjust a pose of an instrument located at the region of interest based on the physical location within the region of interest.

11. The method of claim 10, wherein:
the physical location comprises a 3D position, within the region of interest, of the instrument when the event occurred; and
the adjusting of the pose of the instrument based on the physical location comprises moving the instrument to the 3D position of the physical location within the region of interest.

12. The method of claim 10, further comprising:
detecting, by the tagging system, another interaction, by the user, with the graphical tag element; and
presenting, by the tagging system within the graphical user interface in response to the detection of the another interaction, content associated with the graphical tag element.

13. The method of claim 12, wherein:
the content comprises one or more images of the region of interest captured when the event occurred.

14. The method of claim 13, further comprising:
accessing, by the tagging system, a fluorescence image stream generated based on fluorescence signals detected by an imaging device from the region of interest,
wherein:
the event comprises a determination that a contrast level of a fluorescence image included in the fluorescence image stream is within a predefined range, and
the one or more images includes the fluorescence image.

15. The method of claim 10, wherein the user interaction with the graphical tag element comprises a user selection of the graphical tag element by way of a selector displayed in the graphical user interface.

16. A non-transitory computer-readable medium storing instructions that, when executed, direct at least one processor of a computing device to:
determine, based on medical session data generated by a computer-assisted medical system, that an event occurred at a physical location within a region of interest;
identify, based on the medical session data, the physical location within the region of interest;
render, within a graphical user interface associated with the computer-assisted medical system, a graphical tag element representative of the event and the physical location within the region of interest;
detect a user interaction with the graphical tag element; and
direct, in response to the detecting of the user interaction with the graphical tag element, the computer-assisted medical system to adjust a pose of an instrument located at the region of interest based on the physical location within the region of interest.

17. The computer-readable medium of claim 16, wherein:
the physical location comprises a 3D position, within the region of interest, of the instrument when the event occurred; and
the directing of the computer-assisted medical system to adjust the pose of the instrument based on the physical location comprises directing the computer-assisted medical system to move the instrument to the 3D position of the physical location within the region of interest.

18. The computer-readable medium of claim 16, wherein the instructions, when executed, further direct the at least one processor to:
   detect another interaction, by the user, with the graphical tag element; and
   present, within the graphical user interface in response to the detection of the another interaction, content associated with the graphical tag element.

19. The system of claim 1, wherein the computer-assisted medical system includes the instrument located at the region of interest.

20. The system of claim 1, wherein the event comprises an operation performed at the region of interest by a device associated with the computer-assisted medical system.

* * * * *